(12) United States Patent
Johnson et al.

(10) Patent No.: US 8,972,050 B2
(45) Date of Patent: *Mar. 3, 2015

(54) PHARMACEUTICAL DISPENSING SYSTEMS AND GRAPHICAL USER INTERFACES ASSOCIATED WITH SAME

(75) Inventors: Matthew Johnson, Raleigh, NC (US); Harold Lindsey, Chapel Hill, NC (US); Megan Dunigan, Raleigh, NC (US); Justin Lallinger, Durham, NC (US); John Kirk Hammond, Jr., Raleigh, NC (US)

(73) Assignee: Parata Systems, LLC, Durham, NC (US)

( * ) Notice: Subject to any disclaimer, the term of this patent is extended or adjusted under 35 U.S.C. 154(b) by 1068 days.

This patent is subject to a terminal disclaimer.

(21) Appl. No.: 12/466,717

(22) Filed: May 15, 2009

(65) Prior Publication Data
US 2009/0287347 A1   Nov. 19, 2009

Related U.S. Application Data

(60) Provisional application No. 61/053,921, filed on May 16, 2008, provisional application No. 61/053,735, filed on May 16, 2008, provisional application No. 61/077,661, filed on Jul. 2, 2008, provisional application No. 61/105,529, filed on Oct. 15, 2008.

(51) Int. Cl.
| | | |
|---|---|---|
| G06F 17/00 | (2006.01) | |
| G06F 3/01 | (2006.01) | |
| G07F 11/00 | (2006.01) | |
| G06F 19/00 | (2011.01) | |
| G07F 11/30 | (2006.01) | |
| G07F 11/44 | (2006.01) | |
| G07F 11/62 | (2006.01) | |
| G07F 17/00 | (2006.01) | |

(52) U.S. Cl.
CPC .......... *G07F 11/002* (2013.01); *G06F 19/3462* (2013.01); *G07F 11/30* (2013.01); *G07F 11/44* (2013.01); *G07F 11/62* (2013.01); *G07F 17/0092* (2013.01)
USPC ........................... 700/241; 700/236; 700/244

(58) Field of Classification Search
CPC .................................................. G06F 19/3462
USPC ......................................... 700/236, 241, 244
See application file for complete search history.

(56) References Cited

U.S. PATENT DOCUMENTS

| | | | |
|---|---|---|---|
| 2,002,753 | A | 5/1935 | Parks et al. |
| 2,442,025 | A | 5/1948 | Smith |
| 3,194,431 | A | 7/1965 | Garvin |
| 3,938,700 | A | 2/1976 | Camp et al. |

(Continued)

*Primary Examiner* — Michael K Collins
(74) *Attorney, Agent, or Firm* — Myers Bigel Sibley & Sajovec

(57) ABSTRACT

A pharmaceutical dispensing system includes a frame having first and second opposed sides, a plurality of cells configured to house pharmaceutical pills, a first touch screen display on the frame first side, and a second touch screen display on the frame second side. The pharmaceutical dispensing system includes a processor and memory coupled thereto. A computer program resides in the memory and is executable by the processor for displaying a cell inventory graphical user interface (GUI) within the first touch screen display, and a prescription order processing GUI within the second touch screen display that include status information about a prescription order at a respective stage of completion by the pharmaceutical dispensing system.

17 Claims, 37 Drawing Sheets

(56) References Cited

U.S. PATENT DOCUMENTS

| | | |
|---|---|---|
| 4,232,800 A | 11/1980 | Martin et al. |
| 4,303,179 A | 12/1981 | Spring |
| 4,546,901 A | 10/1985 | Buttarazzi |
| 4,694,230 A | 9/1987 | Slocum et al. |
| 4,740,025 A | 4/1988 | Nelson |
| 4,782,274 A | 11/1988 | Teegarden et al. |
| 4,812,629 A | 3/1989 | O'Neil et al. |
| 5,208,762 A * | 5/1993 | Charhut et al. ............ 700/216 |
| 5,337,919 A | 8/1994 | Spaulding et al. |
| 5,593,267 A * | 1/1997 | McDonald et al. ......... 414/273 |
| 5,720,154 A * | 2/1998 | Lasher et al. ................. 53/411 |
| 5,771,657 A | 6/1998 | Lasher et al. |
| 5,907,493 A * | 5/1999 | Boyer et al. ................. 700/231 |
| 6,202,923 B1 | 3/2001 | Boyer et al. |
| 6,370,841 B1 | 4/2002 | Chudy et al. |
| RE37,829 E | 9/2002 | Charhut et al. |
| 6,522,945 B2 * | 2/2003 | Sleep et al. ................. 700/225 |
| 6,742,671 B2 | 6/2004 | Hebron et al. |
| 6,963,791 B1 * | 11/2005 | Frederick et al. ............ 700/244 |
| 7,228,198 B2 | 6/2007 | Vollm et al. |
| 7,530,211 B2 * | 5/2009 | McErlean et al. ............. 53/505 |
| 7,720,569 B2 * | 5/2010 | Forrester et al. ............. 700/241 |
| 7,783,383 B2 * | 8/2010 | Eliuk et al. ................... 700/245 |
| 7,805,217 B2 * | 9/2010 | Chudy et al. ................. 700/237 |
| 7,860,724 B2 * | 12/2010 | Chudy et al. ...................... 705/2 |
| 7,912,582 B1 * | 3/2011 | Holtje et al. ................. 700/242 |
| 8,215,540 B2 * | 7/2012 | Szesko et al. ................. 235/375 |
| 8,571,886 B2 * | 10/2013 | Chudy et al. ...................... 705/2 |
| 2004/0088187 A1 * | 5/2004 | Chudy et al. ...................... 705/2 |
| 2004/0133705 A1 | 7/2004 | Broussard et al. |
| 2005/0033606 A1 * | 2/2005 | Miller .................................. 705/2 |
| 2006/0161298 A1 * | 7/2006 | DiMaggio ..................... 700/244 |
| 2006/0265102 A1 * | 11/2006 | Bain ............................... 700/237 |
| 2007/0208595 A1 * | 9/2007 | Ohmura et al. ..................... 705/2 |
| 2008/0125897 A1 * | 5/2008 | DiGianfilippo et al. ...... 700/110 |
| 2009/0043421 A1 * | 2/2009 | Parrish et al. ................ 700/241 |
| 2011/0131056 A1 * | 6/2011 | Chudy et al. ...................... 705/2 |

* cited by examiner

REPLENISH CELL WIZARD

1. CELL 1E
2. DRUG 000872772
3. LOT # 1234567
4. LOT EXPIRATION 07/2009
5. ENTER INVENTORY [ ]
6. FILL CELL AND CLOSE CELL DOOR

800

CURRENT INVENTORY:
66
MAXIMUM CAPACITY:
786
MAXIMUM ADDITION:
720

[Keypad: 7 8 9 / 4 5 6 / 1 2 3 / 0 ENTER / < BACKSPACE]

FIG. 17D

NEW CELL WIZARD

1. NEW CELL
2. DRUG          000935211
3. LOT #         qwerty
4. LOT EXPIRATION  02/2010
5. ENTER INVENTORY ADDITION
6. FILL CELL AND CLOSE CELL DOOR

1000

LOT EXPIRATION DATE
- ○ JANUARY (1)      ○ 2008
- ⊘ FEBRUARY (2)     ○ 2009
- ○ MARCH (3)        ⊘ 2010
- ○ APRIL (4)        ○ 2011
- ○ MAY (5)          ○ 2012
- ○ JUNE (6)
- ○ JULY (7)
- ○ AUGUST (8)
- ○ SEPTEMBER (9)
- ○ OCTOBER (10)
- ○ NOVEMBER (11)
- ○ DECEMBER (12)

FIG. 19D

PHARMACEUTICAL DISPENSING SYSTEMS AND GRAPHICAL USER INTERFACES ASSOCIATED WITH SAME

RELATED APPLICATIONS

This application claims the benefit of and priority to U.S. Provisional Patent Application Nos. 61/053,921, filed May 16, 2008, 61/053,735, filed May 16, 2008, 61/077,661, filed Jul. 2, 2008, and 61/105,529, filed Oct. 15, 2008, the disclosures of which are incorporated herein by reference as if set forth in their entireties.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

FIELD OF THE INVENTION

The present invention relates generally to the dispensing of prescriptions of pharmaceuticals and, more particularly, to methods, systems and computer program products for dispensing of pharmaceuticals.

BACKGROUND

Pharmacy generally began with the compounding of medicines, which entailed the actual mixing and preparing of medications. Heretofore, pharmacy has been, to a great extent, a profession of dispensing, that is, the pouring, counting, and labeling of a prescription, and subsequently transferring the dispensed medication to the patient. Because of the repetitiveness of many of the pharmacist's tasks, automation of these tasks has been desirable. Various attempts have been made to automate the pharmacy environment. Different exemplary approaches are shown in U.S. Pat. No. 5,337,919 to Spaulding et al. and U.S. Pat. Nos. 6,006,946; 6,036,812 and 6,1767392 to Williams et al. As automated pharmacy machines have become substantially more robust and complex, operating software that is correspondingly robust is needed to facilitate user interaction and control of these machines.

SUMMARY

In view of the above discussion, a pharmaceutical dispensing system includes a frame having first and second opposed sides, a plurality of cells configured to house pharmaceutical pills, each of the cells being accessible from the first side of the frame for replenishment of pharmaceutical pills therein, and a plurality of chutes, each of the chutes connected to and associated with a respective one of the plurality of cells, each of the chutes being accessible from the second side of the frame for dispensing of pharmaceutical pills. The pharmaceutical dispensing system includes a first touch screen display on the frame first side, and a second touch screen display on the frame second side.

The pharmaceutical dispensing system includes a processor and memory coupled thereto. A computer program resides in the memory that is executable by the processor for displaying a cell inventory graphical user interface (GUI) within the first touch screen display. The cell inventory GUI displays cell inventory information, and includes one or more GUI controls that are responsive to user touching for adding and/or modifying contents of the cells. Also, a computer program resides in the memory that is executable by the processor for displaying a prescription processing GUI within the second touch screen display. The prescription processing GUI comprises status information about a prescription order at a respective stage of completion of the prescription order by the pharmaceutical dispensing system.

The cell inventory GUI displays a graphical representation of each cell. In some embodiments, the graphical representation of each cell is displayed in a color that indicates an inventory level of pharmaceutical pills therein.

The prescription processing GUI displays an array of chute icons. Each chute icon corresponds to a respective chute and displays information about prescription orders for the corresponding chute. For example, each chute icon displays the number of prescription orders in a queue for a corresponding chute, and the number of pills within a prescription order for a respective chute. Each chute icon also displays indicia that indicates when a prescription order is ready in a corresponding chute, and indicia that indicates when a prescription order for a corresponding chute is incomplete. Each of the chute icons is responsive to user touching and, when touched by a user, displays a record for each prescription order in a queue for the corresponding chute. The displayed record includes status information for a respective prescription order, such as prescription order number, drug name, number of pills, prescription processing status, etc. In some embodiments, each prescription order record is displayed with a graphic effect (e.g., color, shading, etc.) that indicates the status of a respective prescription order.

In some embodiments, a border of each chute icon is displayed with a graphic effect (e.g., color, shading, etc.) that indicates the status of a prescription order for a corresponding chute. In some embodiments, each chute icon is displayed with a graphic effect (e.g., color, shading, etc.) that indicates the status of a corresponding chute. In some embodiments, each chute icon expands to an enlarged display size in response to user touching.

In some embodiments, a computer program resides in the memory and is executable by the processor for displaying a report builder GUI within the first and second touch screen displays. The report builder GUI is configured to build reports relating to one or more of the following: pending prescription orders, filled prescription orders, cell inventory information, and drug information.

In some embodiments, a computer program resides in the memory and is executable by the processor for monitoring selected functions of the pharmaceutical dispensing system and for storing selected parameters associated with the monitored functions.

According to some embodiments of the present invention, a GUI for display within a touch screen display of a pharmaceutical dispensing system is configured to display status information about a prescription order at a respective stage of completion of the prescription order by the pharmaceutical dispensing system. The pharmaceutical dispensing system is configured to receive a prescription order and fill a chute with pills according to the prescription order. The GUI includes first and second adjacent portions. An array of chute icons is displayed within the first portion. Each chute icon displays information about prescription orders associated with a corresponding chute and is responsive to user touching. A record for each prescription order in a queue for a corresponding chute is displayed in the GUI second portion in response to user touching a respective chute icon. Each displayed record includes status information for a respective prescription order, such as prescription order number, drug name, number of pills, prescription processing status, etc. In some embodiments, each prescription order record is displayed with a graphic effect (e.g., color, shading, etc.) that indicates the status of a respective prescription order.

In some embodiments, a border of each chute icon is displayed with a graphic effect (e.g., color, shading, etc.) that indicates the status of a prescription order for a corresponding chute. In some embodiments, each chute icon is displayed with a graphic effect (e.g., color, shading, etc.) that indicates the status of a corresponding chute. In some embodiments, each chute icon expands to an enlarged display size in response to user touching.

According to some embodiments of the present invention, a GUI for display within a touch screen display of a pharmaceutical dispensing system is configured to display pharmaceutical pill inventory information. The pharmaceutical dispensing system includes a plurality of cells, and each cell is configured to contain a predetermined number of respective pharmaceutical pills. The GUI displays pharmaceutical pill inventory information for each cell, and at least one GUI control responsive to user touching for adding and/or modifying contents of each of the cells in some embodiments, the pharmaceutical pill inventory information for each cell is displayed in a color that indicates an inventory level of pharmaceutical pills therein.

DETAILED DESCRIPTION

Figure 1:
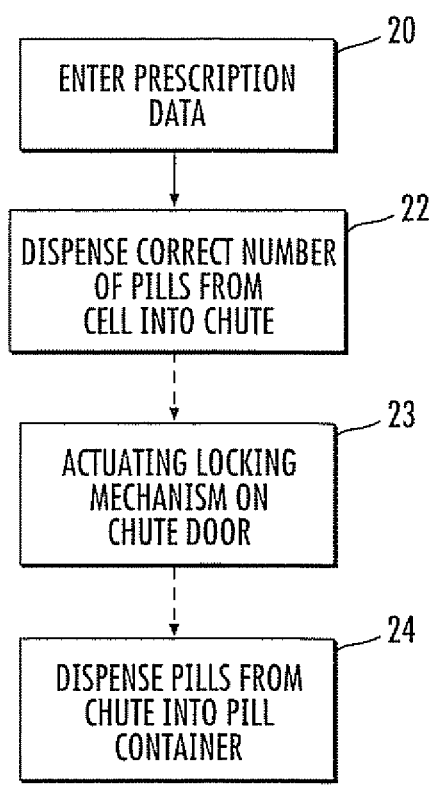
FIG. 1 is a flow chart depicting operations of a pharmaceutical dispensing system according to embodiments of the present invention.

The present invention now will be described more fully hereinafter with reference to the accompanying drawings, in which illustrated embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, steps, operations, elements, and/or components, but do not preclude the presence or addition of one or more other features, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first GUI control could be termed a second GUI control, and, similarly, a second GUI control could be termed a first GUI control without departing from the teachings of the disclosure.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The term "container", as used herein, refers to any type of container including pill containers or vials used to fill a prescription, as well as "stock" bottles that contain pills used to refill cells on the replenishing side of a pharmaceutical dispensing system.

The term "pills" refers to any type of medicament that can be counted and dispensed by a pharmaceutical dispensing system including, but not limited to, capsules, tablets, caplets, gel caps, lozenges, and the like.

The term "wizard", as used herein, refers to a computer utility designed to simplify the execution of lengthy or complicated tasks. As known to those of skill in the art, a wizard is essentially a programmatic method of providing guidance to an operator via GUIs.

The present invention may be embodied as systems, methods, and/or computer program products for carrying out various operations of a pharmaceutical dispensing system. Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), and a portable compact disc read-only memory (CD-ROM).

The present invention is described herein with reference to graphical user interfaces (GUIs), flowchart illustrations and block diagram illustrations of methods, systems, and computer program products for implementing the various operations of a pharmaceutical dispensing system, according to embodiments of the present invention. It will be understood that each block of the flowchart and/or block diagram illustrations, and combinations of blocks in the flowchart and/or block diagram illustrations, may be implemented by computer program instructions and/or hardware operations. These computer program instructions are provided to a processor, or other programmable data processing apparatus to produce a machine, such that the instructions, which execute via the processor and create means for implementing the functions specified in the GUIs, flowcharts and block diagram blocks.

These computer program instructions may also be stored in a computer usable or computer-readable memory such that the instructions produce an article of manufacture including instructions that implement the functions specified in the GUII, flowcharts and block diagram blocks.

The computer program instructions may also be loaded onto a controller or other programmable data processing apparatus to cause a series of operational steps to be performed on the controller or other programmable apparatus to produce a computer implemented process such that the instructions that execute on the controller or other programmable apparatus provide steps for implementing the functions specified in the GUIs, flowcharts, and block diagram blocks.

Referring to FIG. 1, an exemplary process of a pharmaceutical dispensing system 40, according to embodiments of the present invention, is described generally. The process begins with the entry of prescription data (Block 20). The correct number of pills to fill the prescription is dispensed from a cell containing a bulk supply of those pills into an attached chute (Block 22). The pills are then dispensed from the chute into a vial (hereinafter referred to as a pill container) (Block 24), wherein the pill container is typically held by pharmacy personnel. Optionally, the process may include a step in which a door of the chute is unlocked, typically in response to the system providing authorization to an operator to release the pills from the chute (Block 23).

Figure 3:
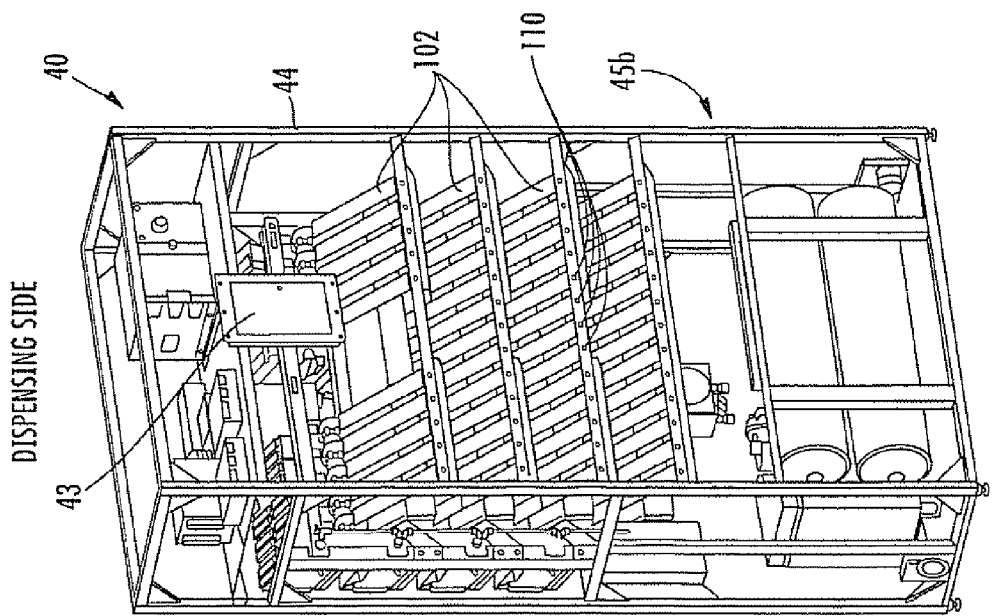
FIG. 3 is a reverse perspective view of the dispensing side (illustrating the chutes) of the pharmaceutical dispensing system of FIGS. 2-3.
Figure 2:
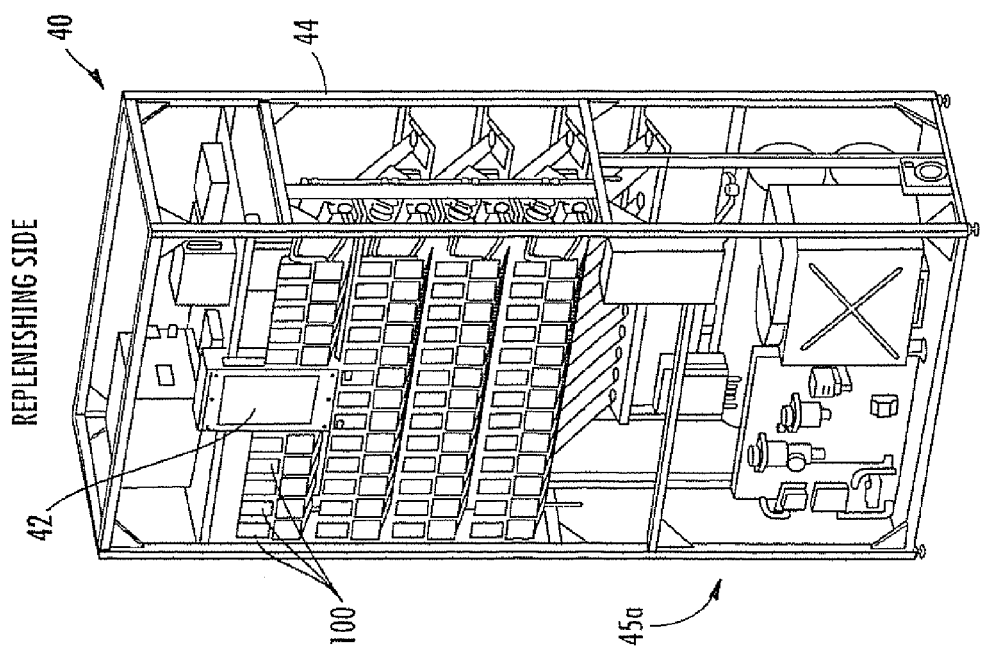
FIG. 2 is a perspective view of the replenishing side (illustrating the cells) of a pharmaceutical dispensing system according to embodiments of the present invention.

A system that can carry out this process is illustrated in FIGS. 2 and 3 and designated broadly therein at 40. The system 40 includes a support frame 44 for the mounting of its various components. The system 40 generally includes as operative stations a controller (represented in FIGS. 2 and 3 by two monitors 42, 43), a number of tablet dispensing cells 100, and a number of chute assemblies 102, each associated with a respective cell 100. As can be seen in FIGS. 2 and 3, the cells 100 are mounted on one side 45a of the frame 44, and the chute assemblies 102 are mounted on the opposite side 45b of the frame 44.

In the illustrated embodiment, the cells 100 are configured to singulate, count and dispense pills through an air agitation technique. The air agitation technique is described in some detail in, for example, U.S. Pat. No. 6,971,541 to Williams et al., supra, and U.S. Pat. No. 7,344,049, and need not be described in detail herein. Those skilled in this art will appreciate that other pill dispensing apparatus, including those that rely on mechanical singulating action (see, e.g., U.S. Pat. No. 7,014,063), may also be employed.

Figure 4:
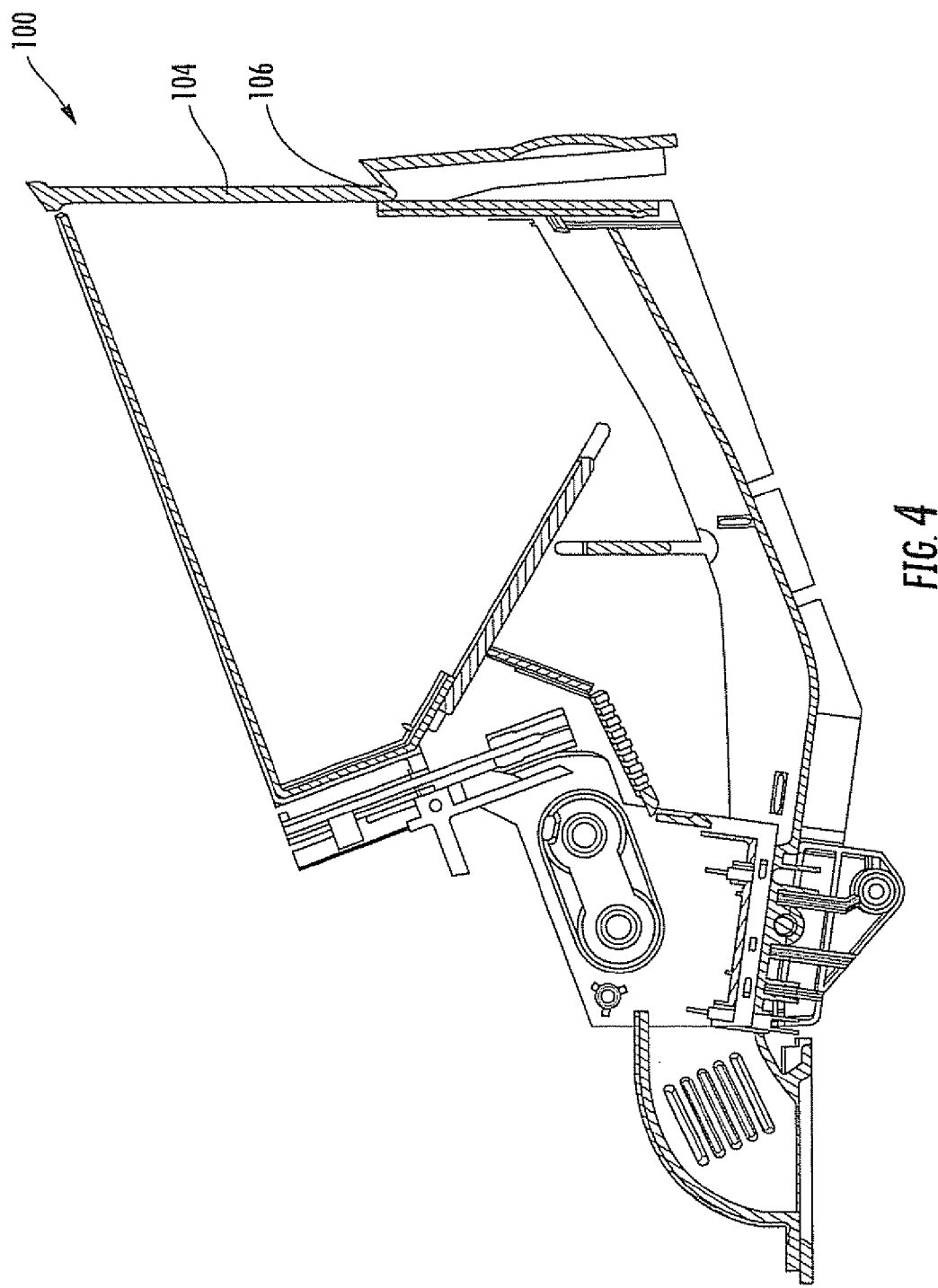
FIG. 4 is a section view of an exemplary cell of the system of FIGS. 2-3.
Figure 5:
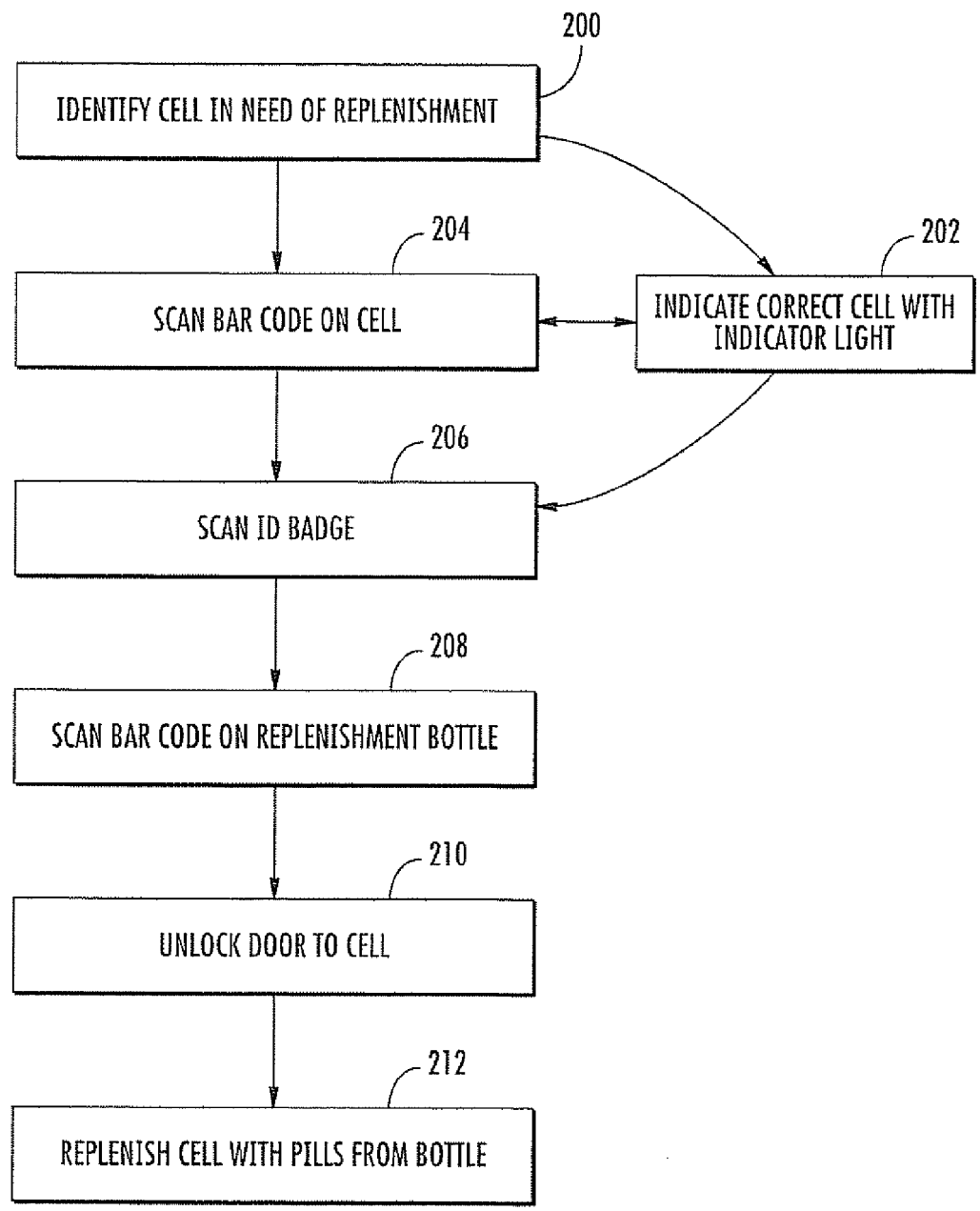
FIG. 5 is a flowchart illustrating the replenishing of cells of the system of FIGS. 2-3.

Referring now to FIG. 4, the cells 100 are oriented so that each can be replenished by an operator facing the side 45a of the frame 44. Each cell 100 includes a door 104 that is pivotally attached to the cell 100 at a hinge 106. During dispensing of pills from the cell 100, the door 104 is in a closed position. If the cell 100 requires replenishment, the door 104 can be moved to an open position that enables an operator to refill the cell 100 with the correct pills.

In some embodiments, each of the cells 100 may have a locking system (such as that illustrated and described in U.S. patent application Ser. No. 11/760,016, filed Jun. 8, 2007, the disclosure of which is hereby incorporated herein in its entirety) that prevents the door 104 from being opened without the scanning of an operator's ID badge or the receipt of replenishment authorization in another form. Each cell 100 may also have a bar code or other identifier (not shown) that indicates the contents of the cell 100. Each of the cells 100 may also have a status light or other indicator (not shown) that indicates a particular cell 100 that is to be replenished in order to direct the operator to the proper cell 100.

Figure 6:
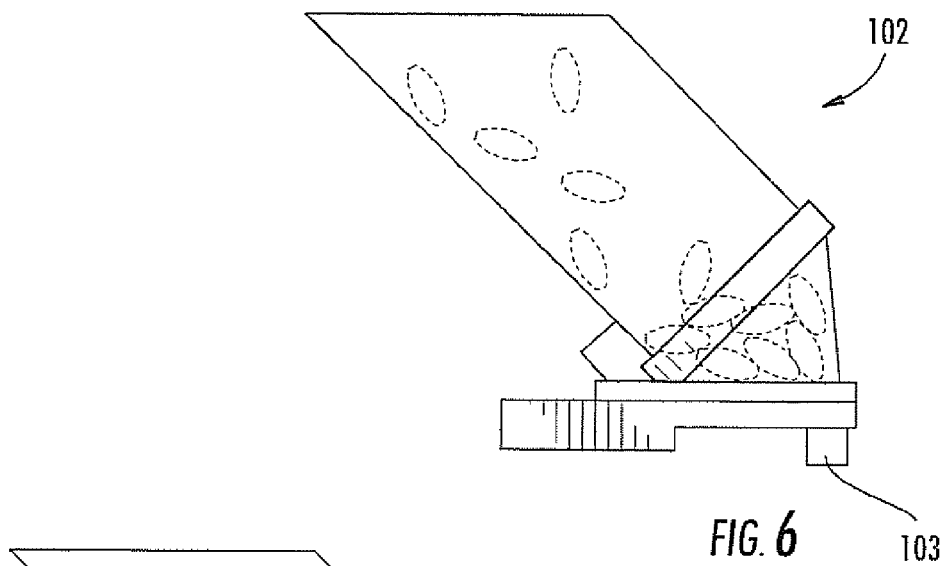
FIG. 6 is a side view of an exemplary chute of the system of FIGS. 2-3 in which pills from a cell are being staged.
Figure 7:
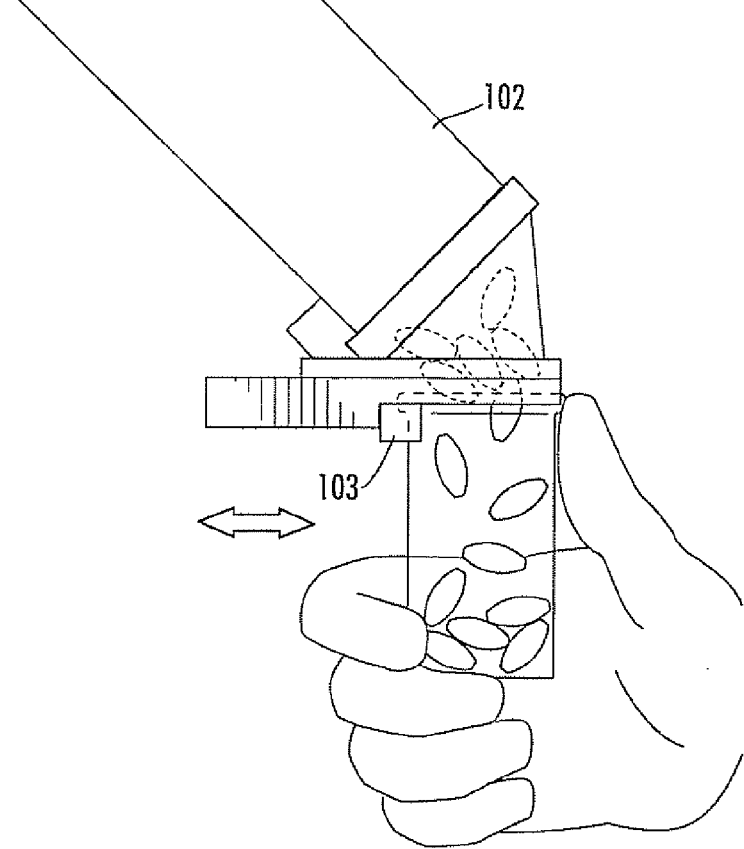
FIG. 7 is a side view of the chute of FIG. 6 illustrating staged pills being dispensed into a pill container.
Figure 8:
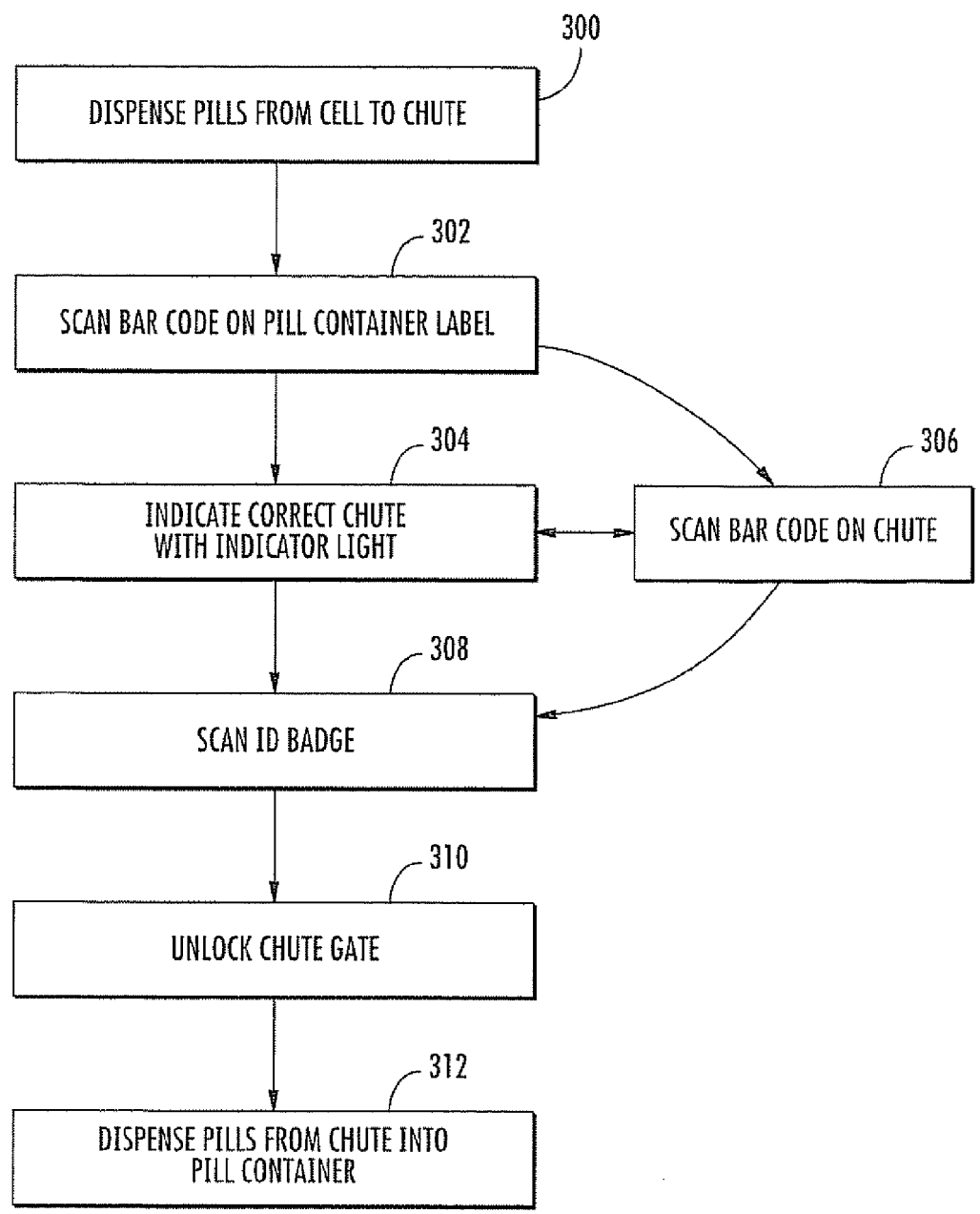
FIG. 8 is a flow chart illustrating the dispensing of pills from chutes of the system of FIGS. 2-3.

Referring now to FIGS. 6 and 7, the chute assemblies 102 extend from the cells 100 on the side 45a to the side 45b, where pills dispensed from a cell 100 into a chute assembly 102 can be dispensed from the chute assembly 102 into a pill container. Each of the chute assemblies 102 includes a door 103, gate or other selective access device at its lower end to allow dispensed pills to be "staged" in the chute assembly 102 after dispensing from the cell 100; subsequently, an operator can open the door 103 to release the pills from the chute assembly 102 into a pill container positioned beneath the door 103 (FIG. 7). Exemplary selective access devices are disclosed in, for example, U.S. Provisional Patent Application No. 60/955,056, filed Aug. 10, 2007; U.S. Provisional Patent Application No. 60/955,059, filed Aug. 10, 2007; U.S. patent application Ser. No. 12/185,981, filed Aug. 5, 2008; U.S. patent application Ser. No. 12/186,025, filed Aug. 5, 2008; U.S. patent application Ser. No. 12/187,666, filed Aug. 7, 2008, entitled SYSTEM AND METHOD FOR DISPENSING OBJECTS; U.S. patent application Ser. No. 12/187,574, filed Aug. 7, 2008, entitled DEVICE FOR STAGING AND DISPENSING TABLETS USEFUL IN SYSTEM AND METHOD FOR DISPENSING PRESCRIPTIONS; and U.S. patent application Ser. No. 12/191,571, filed Aug. 14, 2008, entitled SYSTEM AND METHOD FOR DISPENSING PRESCRIPTIONS, the disclosures of each of which are hereby incorporated herein by reference.

In some embodiments, a bar code scanner or other identifying device may also be included on the side 45b of the frame 44. The bar code scanner can be configured to scan any or all of (a) a bar code on a pill container to identify a specific prescription, (b) an ID badge or other identifier of an operator to verify that the operator has authorization to receive pills from a chute assembly 102, (c) a bar code on a chute assembly 102 to identify the type of pills that are dispensed into that chute assembly 102, or any other item of interest. In some embodiments, the bar code scanner may be replaced with an RFID tag detector and/or, in the case of identifying an authorized operator, a biometric scanner.

In some embodiments, the chute assemblies 102 may include a locking unit (not shown) that prevents the door from being opened without authorization (via a scan of an ID badge, and RFID tag, a biometric identifier, or the like) or without confirmation that it is the correct prescription (via a scan of the bar code on the pill container, for example). An exemplary locking unit is shown in U.S. Provisional Patent Application No. 60/955,056, supra. Also, in some embodiments, the chute assemblies 102 may include a light (not shown) or other indicator (not shown) that indicates which chute assembly 102 contains a given prescription.

According to some embodiments of the present invention, monitors 42 and 43 are touch screen monitors that display graphical user interfaces (GUIs) that allow operators to perform various functions. For example, an operator interacts with graphical representations (e.g., application icons) and controls (e.g., buttons, scroll bars, etc.) collectively referred to herein as GUI controls. These GUI controls perform various functions in response to physical touching by an operator (e.g., touching or tapping via a finger or stylus). GUIs displayed on each side of the pharmaceutical dispensing system 40 relate to tasks that can be performed on the respective sides of the pharmaceutical dispensing system 40. For example, an operator monitors and controls the filling of prescriptions by interacting with GUI controls displayed via the dispensing side monitor 43. An operator performs cell replenishment operations by interacting with GUI controls displayed via the replenishing side monitor 42.

An operator monitors the pharmaceutical dispensing system 40 and interacts with it when initiating certain functions and procedures, e.g., replenishing a cell 100, processing a prescription, etc. According to some embodiments of the present invention, the various GUIs share a common set of functional GUI controls. Moreover, all GUI windows and screens are labeled and employ a consistent "look and feel." In addition, GUI controls related to routine prescription queue management activities are color-keyed and informative. Some GUI controls appear on all toolbars and wizards displayed within the various GUIs. Other GUI controls are context-sensitive.

Instead of employing physical input devices, such as a keyboard, numeric keypad, or mouse, the various GUIs display a virtual keyboard/keypad when one is needed. The operator's finger, in effect, replaces the mouse. According to embodiments of the present invention, the virtual keyboard displayed in various ones of the GUIs includes a filtering function, as will be described below.

The monitor 43, which is located on the dispensing side 45b of the frame 44, displays GUIs which are used to control operations pertaining to dispensing, including the establishment of authorization to dispense pills into a pill container, the locking/unlocking of the doors 103 to chute assemblies 102, the indication of the proper chute assembly 102 for a particular prescription, and the like. The monitor 43 also displays GUIs which are used to control the dispensing of pills from the cells 100 into the chute assemblies 102, either automatically or manually. Dispensing can be the result of manual entry by an operator via one or more GUIs displayed in monitor 43, or can be directed by an external computer, such as an overall pharmacy host computer. The replenishing side monitor 42 displays GUIs which are used to control operations pertaining to replenishment of cells 100, including the need for replenishment, the locking/unlocking of cells 100, the indication of the proper cell 100, confirmation that the correct pills are being added to a cell 100, rejection of incorrect pills, and the like.

The side 45a of the system 40 illustrated in FIG. 2 is referred to as the "inventory side" or "replenishing side." The replenishing side of the system 40 includes an array of cells 100, each of which is configured to store pills of a respective drug. The replenishing side of the system 40 may also include a barcode scanner (not illustrated) for scanning barcodes associated with cells 100 and containers. The system 40 dispenses pills from a cell 100 to fill a particular prescription. GUIs displayed via the monitor 42 on the replenishing side are configured to display various types of information to an operator regarding the status of pill inventory in the various cells 100. In addition, various operator tasks may be performed via GUIs displayed via the replenishing side monitor 42 including, but not limited to, operations associated with replenishing cells 100 with pills, adding a new drug to inventory, setting up parameters of a cell 100, modifying parameters of cells 100, and performing return-to-stock (RTS) operations.

The side 45b of the system 40 illustrated in FIG. 3 is referred to as the "prescription side" or the "dispensing side." The monitor 43 on the dispensing side displays, via various GUIs, information to an operator regarding the status of prescription filling operations (e.g., pending, complete, incomplete, etc.). If a prescription filling operation cannot be completed for some reason, a GUI displays relevant information regarding this via monitor 43. In addition, various operator tasks may be performed via GUIs displayed via the dispensing side monitor 43 including, but not limited to, prescription order monitoring/processing, performing manual prescription filling, scanning out completed prescriptions, resubmitting exceptions, and performing system operations (e.g., configuring cells 100, running diagnostics, etc.).

Dispensing Side GUIs

Prescription processing is monitored and managed from the dispensing side 45b of the system 40. An operator monitors and controls the filling of prescription orders by touching various GUI controls in the GUIs displayed on the dispensing side monitor 43. Dispensing side tasks include prescription order monitoring/processing, performing manual prescription fills, scanning out completed prescriptions, resubmitting exceptions, and performing routine system operations (e.g., configuring cells 100, running diagnostics, etc.).

Figure 9:
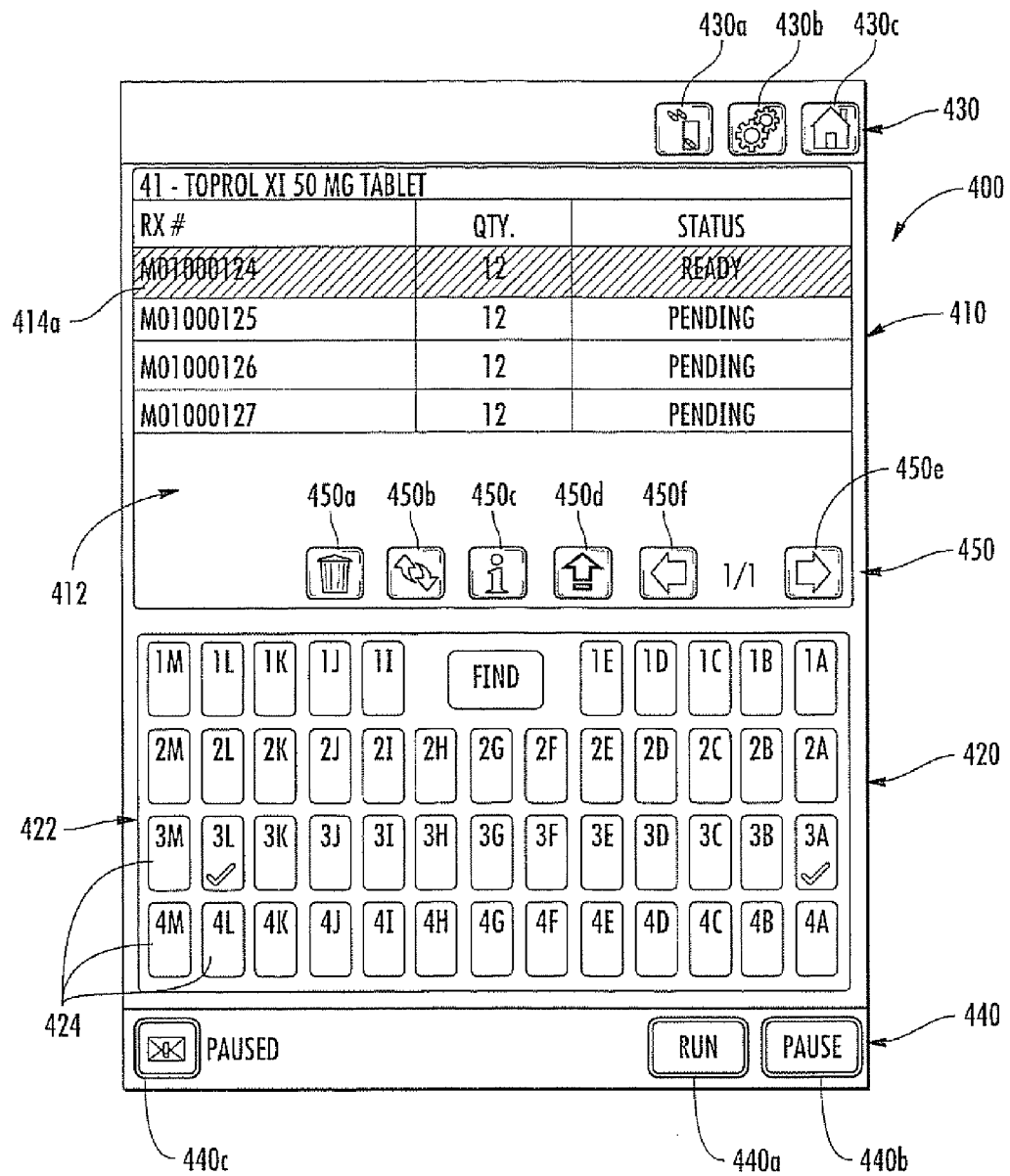
FIGS. 9-11; 12A-12B; 13-16; 17A-17E; 18A-18C; 19A-19F; and 20A-20C are graphical user interfaces (GUIs) that allow an operator of the pharmaceutical dispensing system of FIGS. 2-3 to perform various functions, in accordance with various embodiments of the present invention.

A Home GUI 400, illustrated in FIG. 9, is utilized for prescription monitoring and prescription queue management activities. The illustrated Home GUI 400 has an upper section 410 and a lower section 420. The upper section 410 displays the Chute Details window 412, which identifies the prescription order(s) currently in each chute's queue, the status of each prescription order (e.g., Ready, Hold, Pending or Incomplete), drug name and chute/cell ID, prescription number and pill quantity. A record for each prescription order for a respective chute 102 is displayed within the Chute Details window 412. In some embodiments, the color of each displayed prescription record in the Chute Details window 412 communicates the status (pending, complete, on hold, etc.) of the prescription order. For example, green may indicate a prescription order is ready, light blue may indicate a prescription order is currently being filled, white may indicate that a prescription order is pending or on hold, and red may indicate that a prescription order is incomplete. For example, in the illustrated embodiment, prescription order record 414a may be displayed in green to indicate that the prescription order associated with prescription order record 414a is ready (i.e., that a chute 102 contains pills that are ready to be dispensed into a pill container pursuant to a prescription order). Embodiments of the present invention, however, are not limited to any particular colors for indicating prescription order status. Various colors, as well as shadings and other graphic effects, may be utilized, without limitation.

The lower section 420 of the illustrated Home GUI 400 displays the Main Chute Grid 422, which provides information about each chute 102, including a chute's status and current pill quantity. The Main Chute Grid 422 includes an array of chute icons 424, each chute icon 424 corresponding to a particular chute 102 of the pharmaceutical dispensing system 40. The displayed array of chute icons 424 corresponds to the physical array of actual chutes 102 of the pharmaceutical dispensing system 40. In other words, the chute icons 424 are arranged in the same number of rows and columns as the actual chutes 102 in order to facilitate easy location of a chute 102 by an operator.

Figure 10:
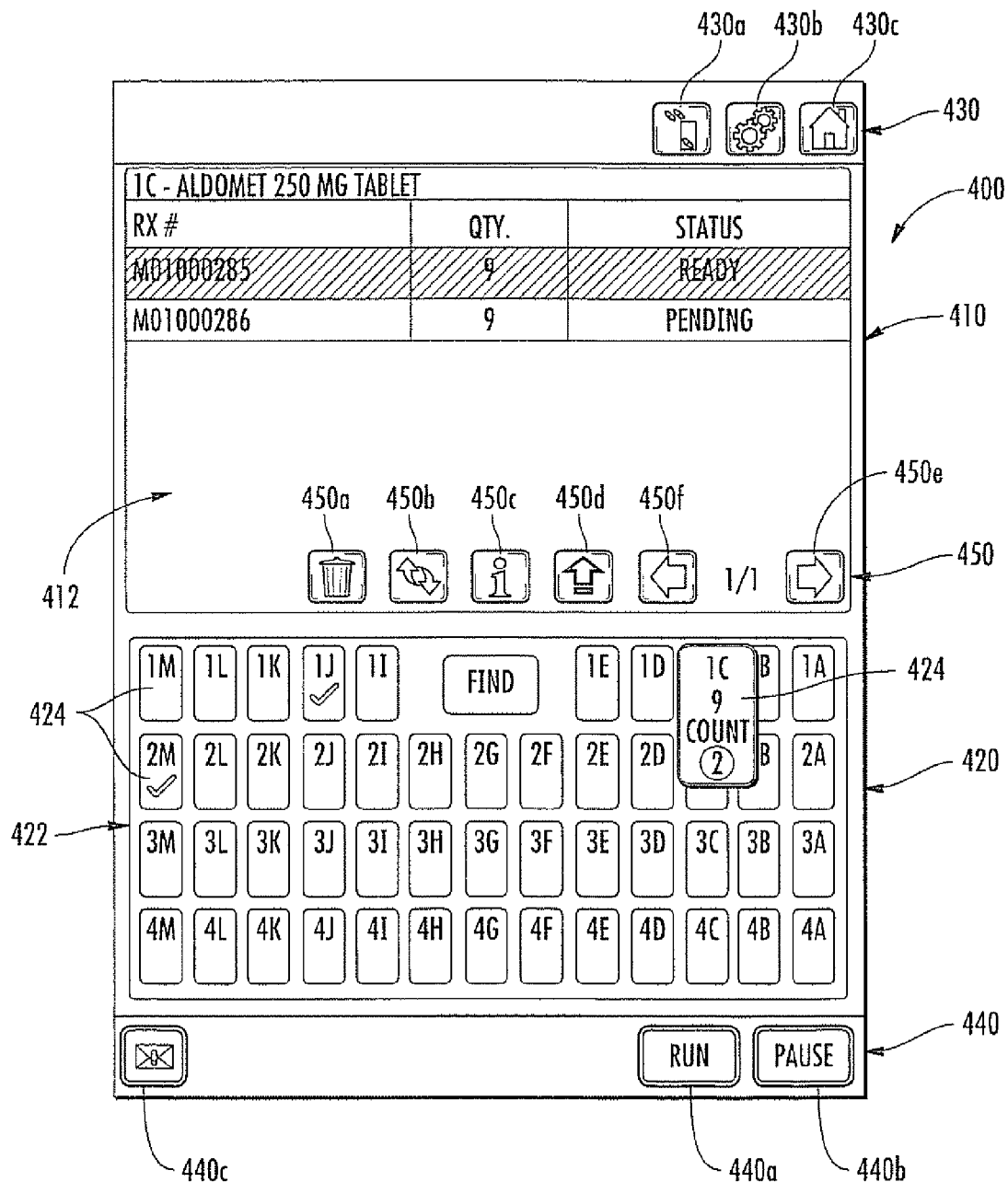

Each chute icon 424 in the Main Chute Grid 422 is responsive to user touching for displaying information about a particular chute 102. When a chute icon 424 is touched, its displayed size is expanded within the Main Chute Grid 422 to display additional information, as illustrated in FIG. 10. When a chute icon 424 is in an expanded display, a graphic effect (e.g., color, shading, glow, blur, etc.) of the border indicates the status of a prescription order for the chute 102. In addition, the expanded chute icon 424 displays the number of pills contained within the chute 102, and the number of prescription orders in the queue for the particular chute 102. Touching any of the chute icons 424 for active chutes 102 also displays, within the Chute Details window 412, a prescription order record for each prescription order for the corresponding chute 102.

Referring back to FIG. 9, the Home GUI 400 has an upper main toolbar 430 and a lower main toolbar 440. GUI controls included in the upper main toolbar 430 include Manual Fill GUI control 430a, System Functions GUI control 430b and Home GUI control 430c. Manual Fill GUI control 430a, when touched by an operator, allows the operator to enter a prescription order into the pharmaceutical dispensing system 40 manually (rather than it being sent to the system 40 automatically, such as from a pharmacy host system). Upon activating GUI control 430a, a manual fill wizard is launched that guides an operator through a process for manually filling a prescription order. System Functions GUI control 430b allows an operator to display and/or configure various parameters of the pharmaceutical dispensing system 40. Home GUI control 430c, when touched by an operator, displays the Home GUI 400.

GUI controls included in the lower main toolbar 440 include Run GUI control 440a, Pause GUI control 440b, and Open Message Queue GUI control 440c. An operator touches the Run GUI control 440a to process and fill prescription orders. In "Run" mode, pending prescription orders are filled (e.g., chutes 102 are filled with pills from respective cells 100 pursuant to a prescription order). An operator touches the Pause GUI control 440b to suspend prescription order processing. In "Pause" mode, prescription orders can be submitted to the pharmaceutical dispensing apparatus 40, but are not filled until the Run GUI control 440a is touched. The Open Message Queue GUI control 440c, when touched by an operator, opens the alert message queue. Open Message Queue GUI control 440c is displayed automatically when there is a message. The alert message queue contains messages generated by the pharmaceutical dispensing system 40, for example, error messages that relate to system-level problems such as with filling prescriptions, etc. Touching the Open Message Queue GUI control 440c displays a list of the most recent alert messages (e.g., up to five, etc.) issued by the pharmaceutical dispensing apparatus 40.

The illustrated Home GUI 400 also has a taskbar 450 that contains context-sensitive GUI controls 450a-450f. These GUI controls 450a-450f are enabled only when their functions can be performed on a currently selected prescription order record in the Chute Details window 412. Delete GUI control 450a deletes a selected prescription order. For example, to delete or cancel a pending prescription order from the pending queue, an operator selects a pending prescription order record in the Chute Details window 412 and then touches GUI control 450a to delete the prescription order.

Retry GUI control 450b resubmits a prescription order. This is used mainly to retry running/waiting prescription orders that are incomplete for some reason (e.g., a cell 100 is out of pills, etc.), or because some error occurred in the pharmaceutical dispensing system 40. In operation, a prescription order record displayed in the Chute Details window 412 is selected. The operator then touches GUI control 450b to resubmit the selected prescription order for processing.

Details GUI control 450c displays detail information about incomplete (and complete) prescription orders. For example, when a prescription order record displayed within Chute Details window 412 is selected, an operator then touches GUI control 450c to display information about the selected prescription order. Advance GUI control 450d moves a prescription order to the top of the queue for a particular chute 102. For example, when a prescription order record displayed within Chute Details window 412 is selected, an operator can touch GUI control 450d to advance the selected prescription order to the top of the displayed queue.

The Chute Details window 412 only displays a certain number of prescription order records at a time. The Next/Last GUI controls 450e, 450f allow an operator to move forward and backward, respectively, through multiple pages of displayed records.

Figure 11:
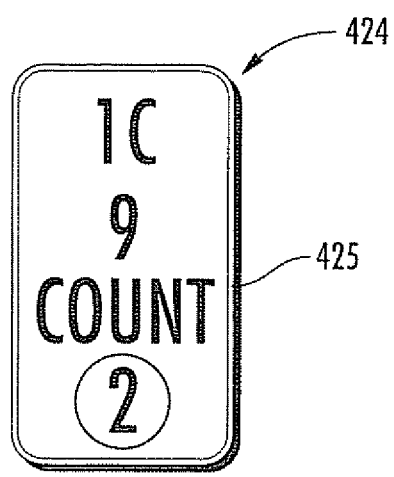

FIG. 10 illustrates the Home GUI 400 wherein an operator has touched a chute icon 424 for a particular chute 102. The chute icon 424 has expanded its display size within the Main Chute Grid 422, as illustrated. The expanded chute icon 424 corresponds to a chute with the ID of "1C" and indicates that nine (9) pills are in chute 1C, and that there are two (2) prescriptions in the queue for chute 1C. An enlarged view of the expanded chute icon 424 is illustrated in FIG. 11. The border 425 has a color (or other graphic effect, such as shading, etc.) that indicates the status of a prescription order for chute 1C (e.g., red for incomplete prescription orders, green for complete prescription orders, etc.).

Referring back to FIG. 9, in some embodiments, chute icons 424 displayed within the Main Chute Grid 422 are displayed in colors (or other graphic effects, such as shading, etc.) to indicate the status of corresponding chutes 102. For example, non-configured chutes 102 (i.e., chutes that are not being used to fill prescription orders) may have corresponding chute icons 424 that are black. Active chutes 102 are chutes that are currently being used to fill prescription orders, and may have corresponding chute icons 424 that are white. Inactive chutes 102 are chutes that are configured to be used to fill prescription orders, but that are not currently being used to fill prescription orders. Inactive chutes 110 may have corresponding chute icons 424 that are grey. Accordingly, an operator can quickly and accurately learn the status of all chutes 102 of the pharmaceutical dispensing system 40 by viewing the Main Chute Grid 422 in Home GUI 400.

Figure 12A:
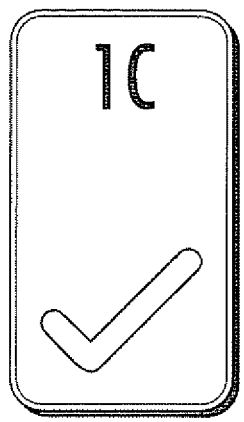
Figure 12B:
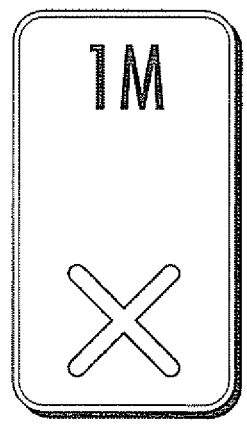

Chute icons 424 within the Main Chute Grid 422 may also include a "check mark" or an "X mark" (FIGS. 12A-12B). Checkmarks and X marks may be color-coded (e.g., checkmarks may be green and X marks may be red, etc.). A checkmark means the chute 102 represented by the chute icon 424 contains a prescription order that is ready. An X mark means that the chute 102 represented by the chute icon 424 contains an incomplete prescription order. For example, as illustrated in FIG. 12A, chute "1C" contains a prescription order that is ready. As illustrated in FIG. 12B, chute "1M" contains an incomplete prescription order.

When an operator touches a prescription order record in the Chute Details window 412, context-sensitive GUI controls 450a-450f in the taskbar 450 are activated. For example, if a selected prescription order record is for an incomplete prescription order, the Retry GUI control 450b is activated so that the operator has the option to rerun the prescription order. The Details GUI control 450c is also activated so that the operator can display additional information to help remedy an error condition that caused the incomplete prescription order.

As a prescription order is processed and filled by the pharmaceutical dispensing system 40, its status is displayed in the Status column of the Chute Details window 412. A "pending" status is assigned to all prescription orders when first received from a pharmacy's computer. A "hold" status is assigned to all prescription orders received from a pharmacy's computer when the "On Demand" option is enabled. "On Demand" is a function of the pharmaceutical dispensing system 40 that allows individual prescription orders to be expedited and filled. When "On Demand" is enabled, all prescription orders received from a pharmacy's computer initially are assigned a processing status of "hold." Once the corresponding prescription order record is selected for a prescription order with a "hold" status, the prescription order can be moved to the top of the queue for a chute 102 by using the Advance GUI control 450d. If "On Demand" is disabled, prescription orders received from a pharmacy's computer are assigned a state of "pending" and are processed automatically on a "first in, first out" basis.

A "waiting" status indicates that a prescription order is at the top of the queue for a particular chute 102 and the pharmaceutical dispensing system 40 is preparing to process the prescription order. A "counting" status indicates that the pills for a prescription order are being counted and currently being dispensed into a chute 102. A "ready" status indicates that pill counting is complete and the pills are in the chute 102, ready to be dispensed into a pill container by the operator. A prescription order has a "complete" status when the pills for the prescription order have been cleared from a chute 102 (i.e., an operator has dispensed the pills from a chute 102 into a pill container). In some embodiments of the present invention, the word "complete" does not actually appear in the status column of the Chute Details window 412. Completed orders can be tracked using the Reports component of the pharmaceutical dispensing system 40, as described below. An "incomplete" status indicates that a prescription order was not filled successfully by the pharmaceutical dispensing system 40.

Various other functions can be performed via the Chute Details window 412. For example, an operator can locate and unlock a chute 102 for a particular prescription order. Details regarding an incomplete prescription order (e.g., insufficient pill quantity, etc.) can be displayed via the Details GUI control 450c. An incomplete prescription order can be rerun by the pharmaceutical dispensing system 40 via the Retry GUI control 450b. A prescription order can be cancelled by removing the corresponding prescription order record from the Chute Details window 412 via the Delete GUI control 450a.

Replenishing Side GUIs

Figure 13:
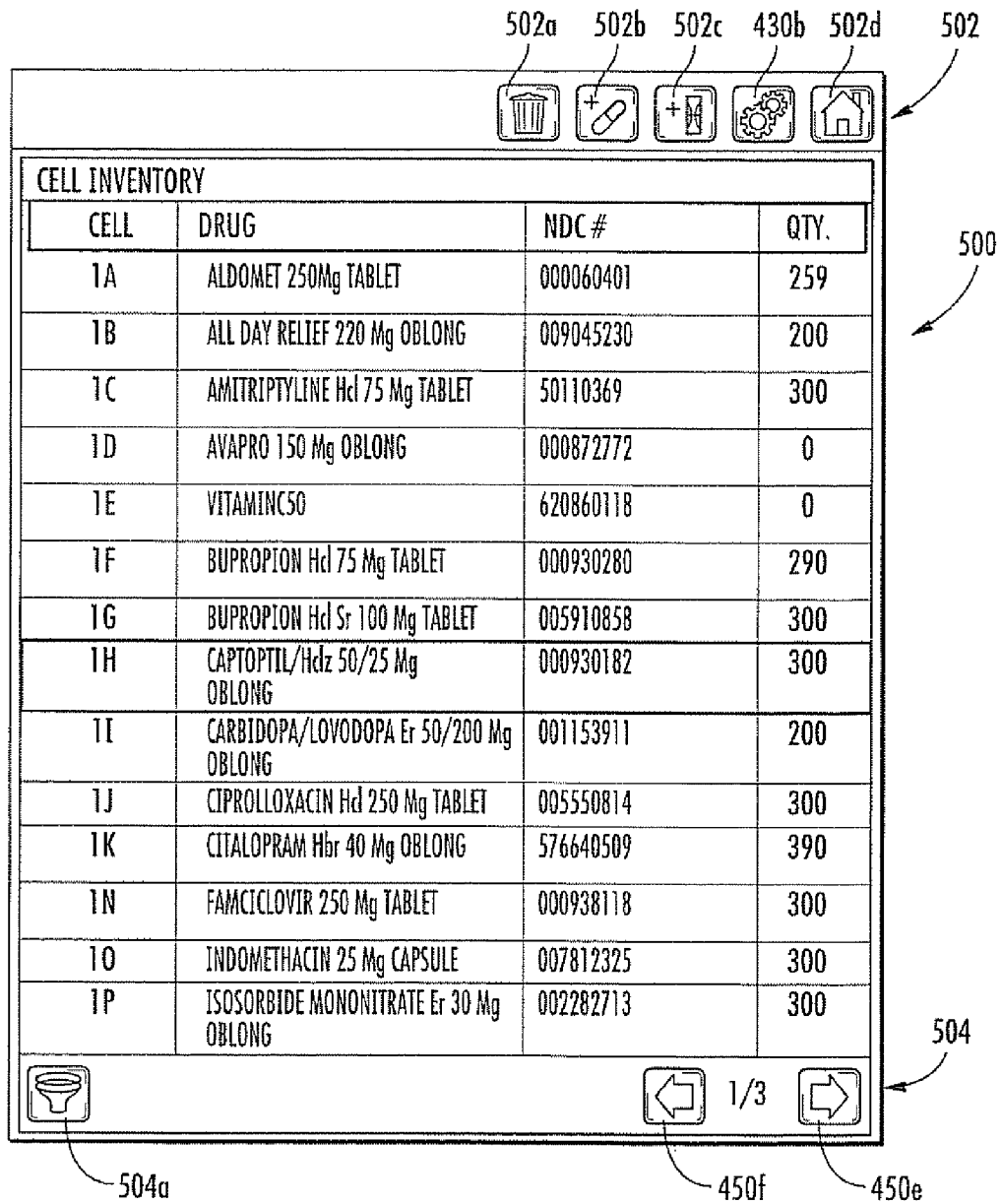

Referring now to FIG. 13, a Cell Inventory GUI 500 is illustrated. The Cell Inventory GUI 500 is considered the "Home GUI" for the replenishing side of the pharmaceutical dispensing system 40. The Cell Inventory GUI 500 displays information about the contents of cells 100 on the replenishing side 45a of the pharmaceutical dispensing system 40 that are currently calibrated to contain a particular drug. For example, the Cell Inventory GUI 500 displays the following information about each cell 100: cell location, drug contained within cell, NDC (National Drug Code) information, and drug quantity in each cell. As known to those skilled in the art, drug products are identified and reported using a unique, three-segment NDC number, which is a universal product identifier for human drugs.

The illustrated Cell Inventory GUI 500 has an upper main toolbar 502 and a lower main toolbar 504. GUI controls in the upper main toolbar 502 include Delete Cell GUI control 502a, New Drug GUI control 502b, New Cell GUI control 502c, Systems Functions GUI control 430b, and Home GUI control 502d. Systems Functions GUI control 430b is the same GUI control as described above with respect to the Home GUI 400 (FIG. 9) for the Dispensing side of the pharmaceutical dispensing system 40. The Delete Cell GUI control 502a allows an operator to delete a cell 100 from a database of the pharmaceutical dispensing system 40.

The Cell Inventory GUI 500 serves as the launching point for various wizards, including a Replenish wizard, an RTS wizard, a New Cell wizard, and a New Drug wizard, etc. The wizard GUI controls appear in the upper main toolbar 502. For example, the New Drug GUI control 502b launches a New Drug wizard that is used by an operator when adding a new drug to the inventory of the pharmaceutical dispensing system 40, as will be described below. The New Cell GUI control 502c launches a New Cell wizard that is used by an operator when setting up a new cell 100, as will be described below. The Home GUI control 502d displays the Cell Inventory GUI 500.

Figure 16:
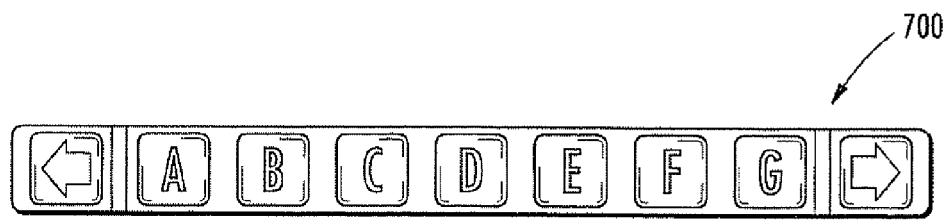
Figure 17A:
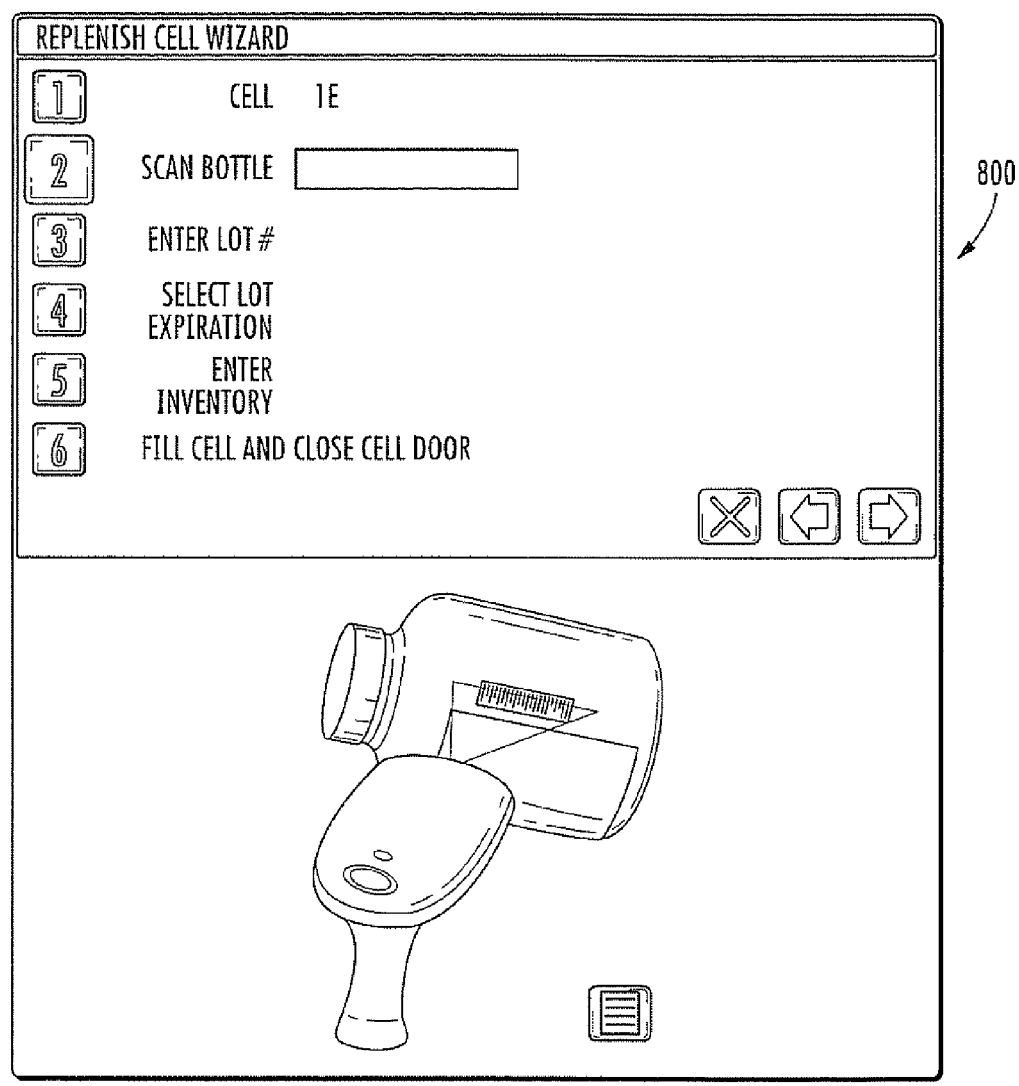
Figure 17B:
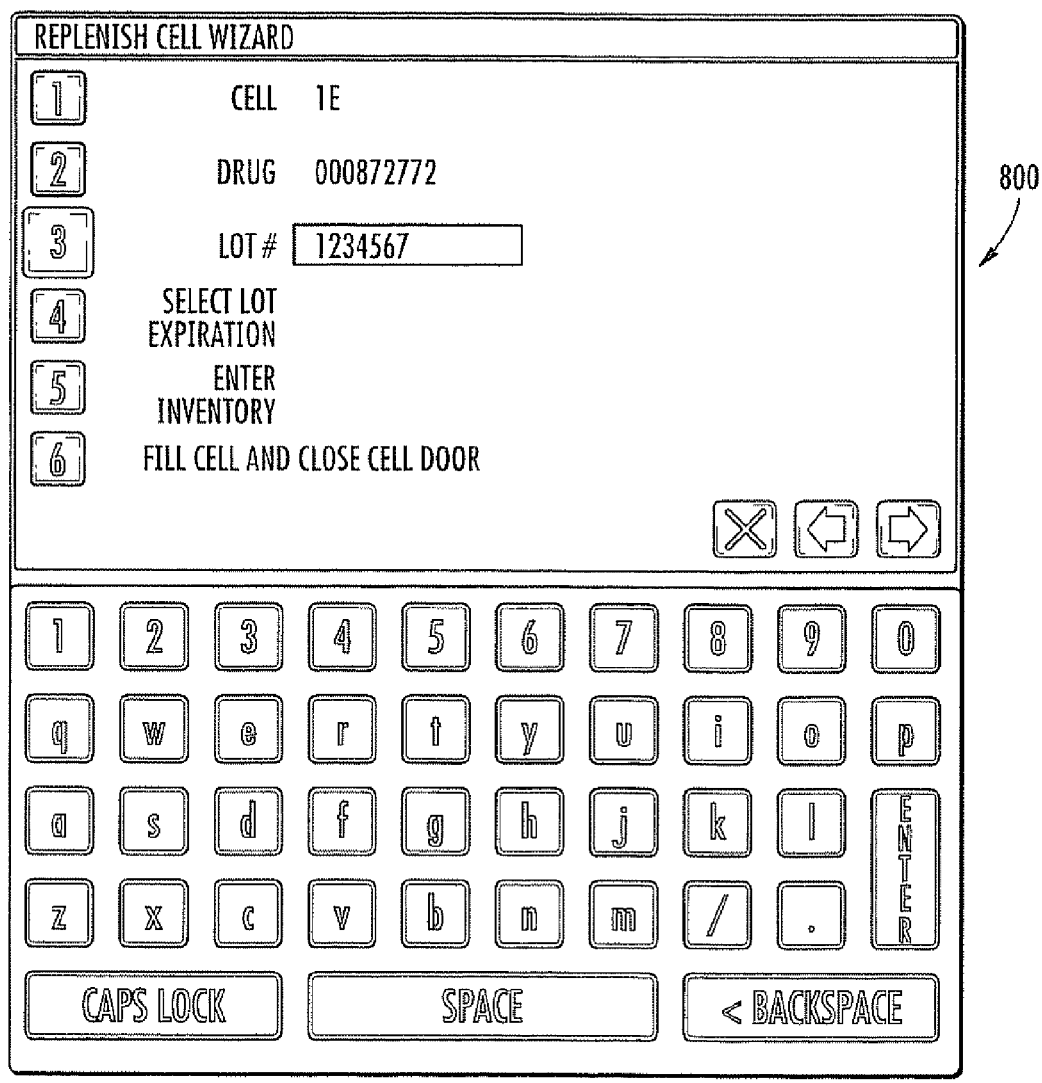
Figure 17C:
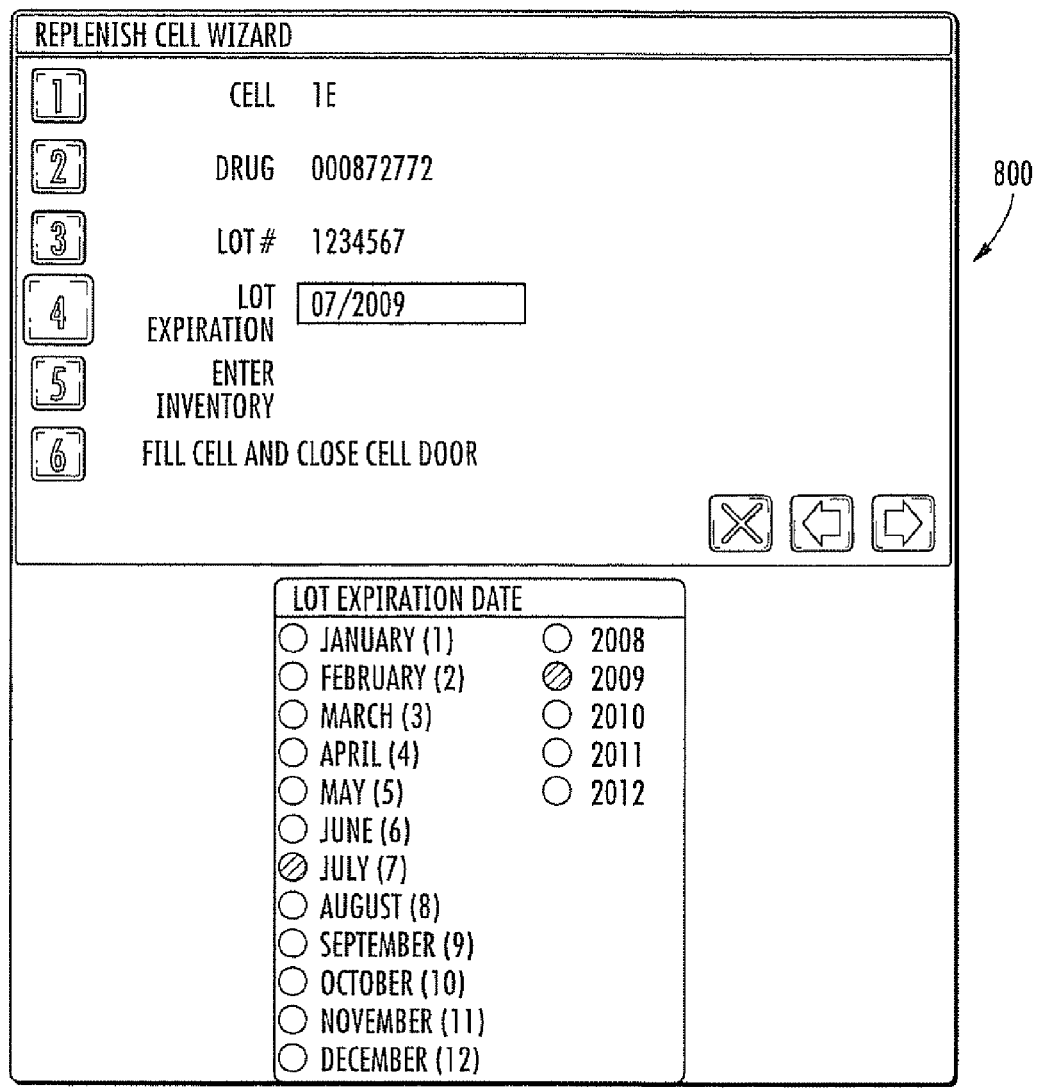
Figure 17E:
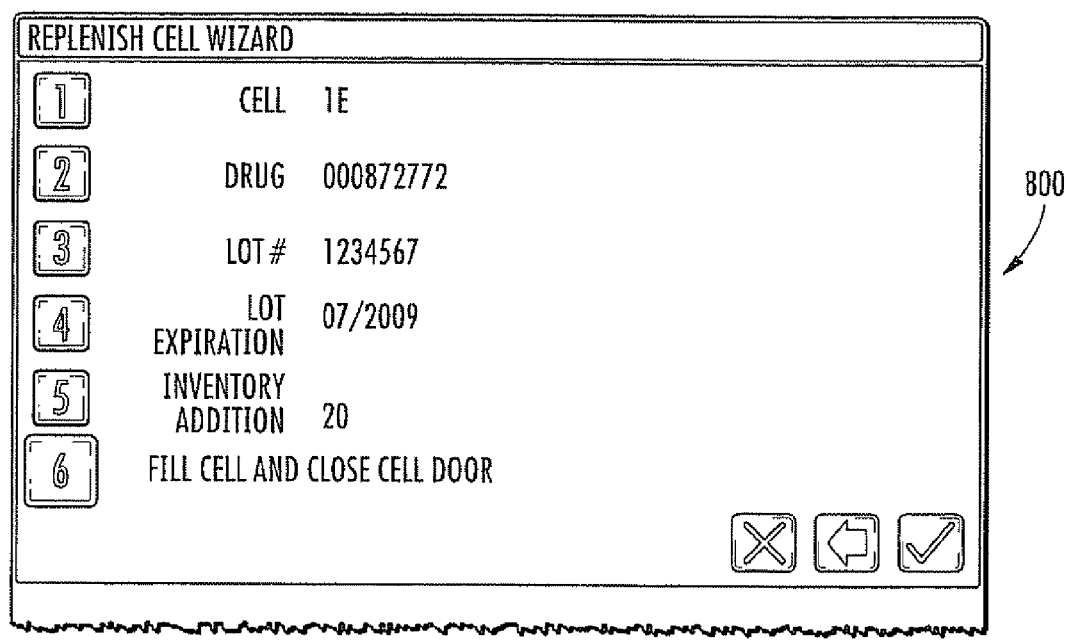

GUI controls in the lower main toolbar 504 include a Filter GUI control 504a and Next/Last GUI controls 450e, 450f. Filter GUI control 504a allows an operator to filter displayed information via a filter keyboard 700 (FIG. 16). The Filter GUI control 504a allows an operator to quickly display information that matches a filtering key selected from the filter keyboard 700. For example, using the filtering keypad 700, an operator can find specific information (e.g., a drug name, patient surname, etc.) with the fewest number of keystrokes needed to identify and display the information. For example, if an operator wanted to display all drug names beginning with the letter "C", the operator would touch the letter "C" on the filter keypad 700. In some instances, filtering may be performed automatically. For example, when an operator initiates an RTS procedure by scanning a pill container, the information in the Cell Inventory GUI 500 (FIG. 13) is automatically filtered. In other words, the Cell Inventory GUI 500 displays only the record for the cell that dispensed the prescription order. Next/Last GUI controls 450e, 450f allow an operator to move forward and backward, respectively, through multiple pages of displayed information.

The Cell Inventory GUI 500 displays cell inventory information in read-only mode. The displayed information can be filtered and/or sorted. For example, only cells containing a certain drug can be displayed, etc.

In the Cell Inventory GUI 500, cells that are either empty or contain pills below a "low Inventory" level (e.g., less than 50 pills, etc.) are shaded, for example in yellow, so that they are brought to the attention of the operator. Each cell 100 of the pharmaceutical dispensing system 40 includes a status indicator, such as light emitting diode (LED). Touching any row displayed in the Cell Inventory GUI 500 causes a status indicator for the corresponding cell 100 to flash for a predetermined duration, for example 15 seconds. The status indicator allows the operator to quickly locate the cell 100 on the replenishing side of the system 40. Scanning a pill container or stock bottle on the replenishing side of the pharmaceutical dispensing system 40 displays the location of the cell containing the corresponding drug.

Figure 14:
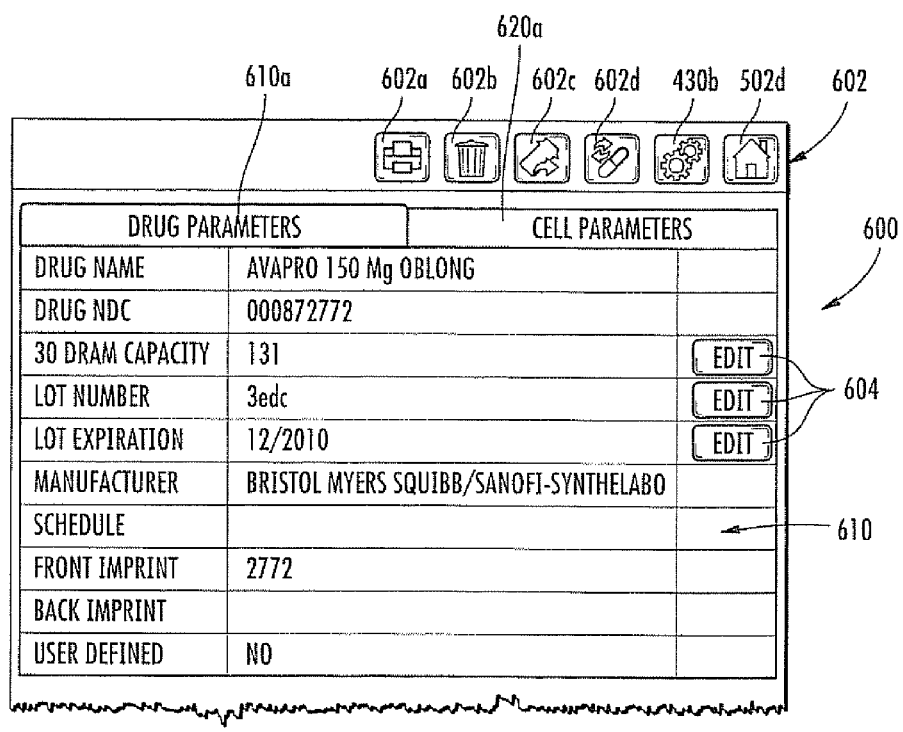
Figure 15:
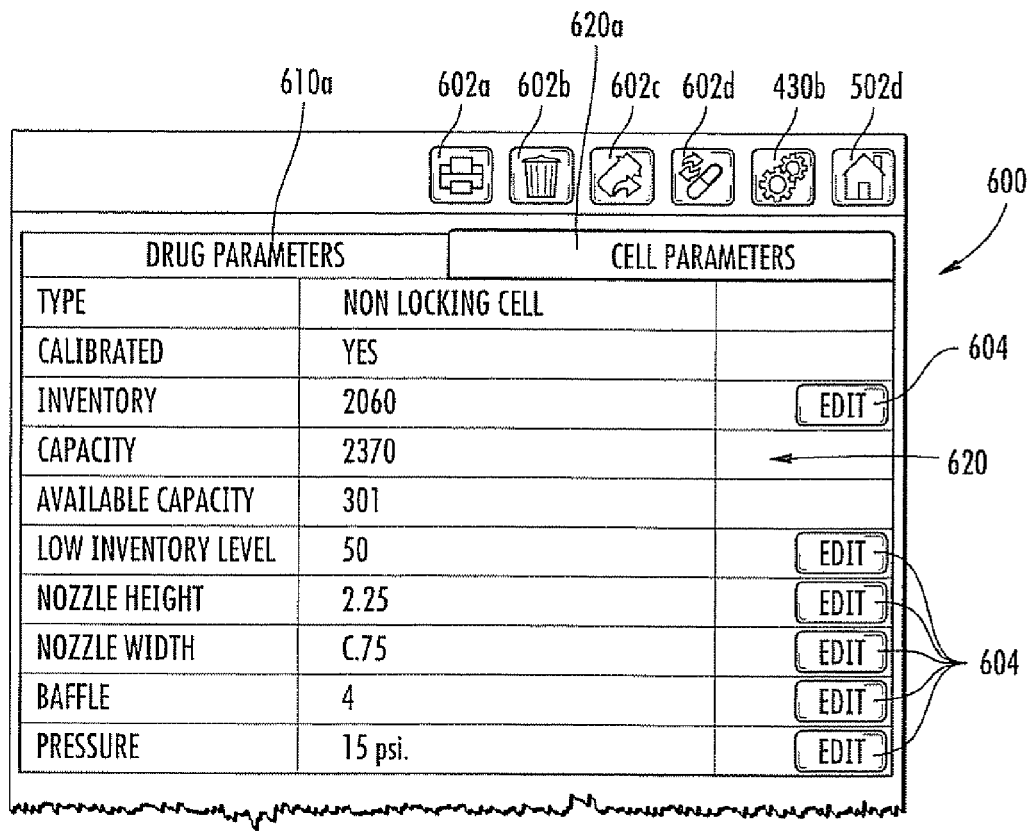

Referring to FIG. 14, a Parameters GUI 600 is illustrated that displays information about a particular cell 100 and a drug contained within the cell 100. The Parameters GUI 600 is configured to display a Drug Parameters GUI 610 and a Cell Parameters GUI 620 (FIG. 15). Drug Parameters GUI 610 is displayed by an operator touching Drug Parameters tab 610*a*, and the Cell Parameters GUI 620 is displayed by an operator touching the Cell Parameters GUI 620*a*. An operator can add/modify certain drug and cell settings and values (e.g., air pressure, and other dispensing values) via these two GUIs.

The Parameters GUI 600 includes an upper main toolbar 602. GUI controls in the upper main toolbar 602 include Print GUI control 602*a*, Delete Cell GUI control 602*b*, Return to Stock (RTS) GUI control 602*c*, Replenish Cell GUI control 602*d*, Systems Functions GUI control 430*b*, and Home GUI control 502*d*. The Print GUI control 602*a* allows an operator to print labels for cells 100. The Delete Cell GUI control 602*b* allows an operator to delete a cell (i.e., the particular cell 100 for which the Parameters GUI 600 is currently displayed) from a cell database of the pharmaceutical dispensing system 40. The RTS GUI control 602*c* launches an RTS wizard which allows an operator to return dispensed pills to a cell 100. The Replenish Cell GUI control 602*d* launches a Replenish Cell wizard that allows an operator to restock the pill inventory of a cell 100. The Home GUI control 502*d* displays the Cell Inventory GUI 500. The Systems Function GUI control 430*b* is the same GUI control as described above with respect to the Home GUI 100 (FIG. 9) of the Dispensing side of the pharmaceutical dispensing system 40.

The Parameters GUI 600 is accessed by scanning a cell (i.e., scanning a barcode attached to a cell 100 via a barcode scanner associated with the Replenishing side of the pharmaceutical dispensing system 40). The Parameters GUI 600 displays the current settings for the scanned cell and for the drug the cell is configured to dispense. For example, in the illustrated Drug Parameters GUI 610 displayed in FIG. 14, parameter information displayed about the drug within a specific cell 100 includes drug name, NDC, lot number, lot expiration, manufacturer, and various other information. Some of these parameters can be modified by an operator via an Edit GUI control 604. In the illustrated Cell Parameters GUI 620 (FIG. 15), parameter information displayed about the cell includes type of cell, capacity, low inventory level, and various other information. Some of these parameters can be modified by an operator via an Edit GUI control 604.

Replenish Wizard

There are several occasions when an operator needs to add drugs to one or more of the cells 100. For example, a cell 100 that is empty or whose pill inventory is low needs to be replenished. In addition, when a new drug is added to the pharmaceutical dispensing system 40 one or more cells 100 need to be replenished. Cell replenishment is performed from the replenishing side of the pharmaceutical dispensing system 40. Drug replenishment can occur at any time, including when the pharmaceutical dispensing system 40 is in run mode and processing prescription orders.

The Replenish wizard 800 is illustrated in FIGS. 17A-17E and is launched via Replenish Cell GUI control 602*d*. The various steps of replenishing a cell 100 are numbered on the left hand side of the various replenish wizard GUIs, as illustrated (FIGS. 17A-17E). To replenish a cell 1001 the following steps are performed. The stock bottle of the drug to be replenished is retrieved and the cell to be replenished is located. On the Cell Inventory GUI 500, an operator touches the Replenish Wizard GUI control 602*d*. The replenish wizard appears and the operator is directed to scan the NDC barcode on the stock bottle to verify that the correct drug is being added to a cell 100 via a barcode scanner associated with the pharmaceutical dispensing system 40. Alternatively, a pop-up keyboard may be used to enter the NDC number manually. The operator then enters the lot number on the stock bottle using the pop-up keypad. The operator then touches the stock bottle expiration GUI control and selects the month/year from the month/year drop-down list. The operator then touches the add GUI control and enters the number of pills to be added to the cell 100 using the pop-up keypad. The operator then adds pills to the cell 100, closes the cell door and touches the complete GUI control.

Return-to-Stock Wizard

Figure 18A:
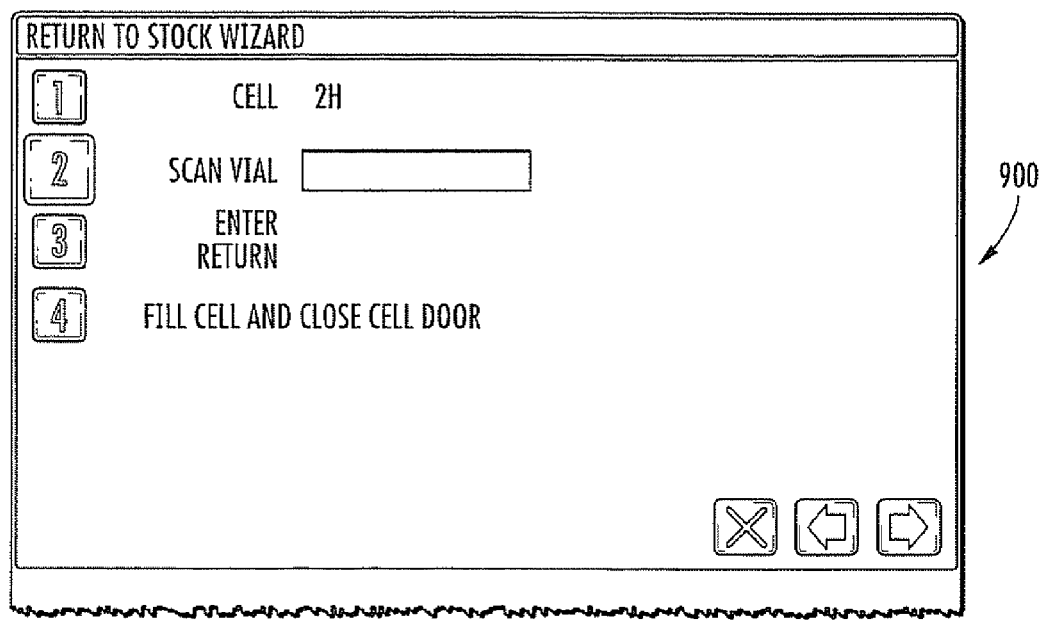
Figure 18B:
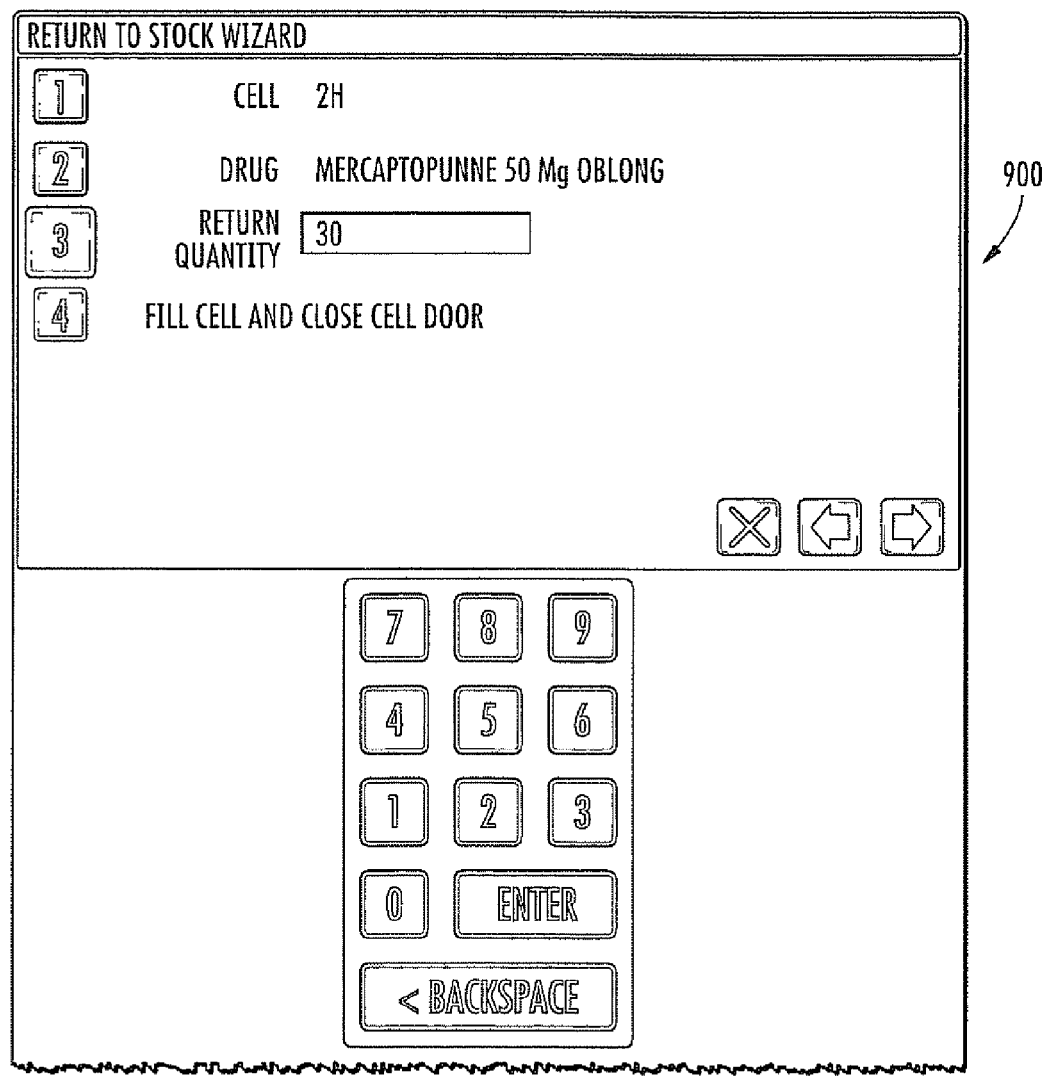
Figure 18C:
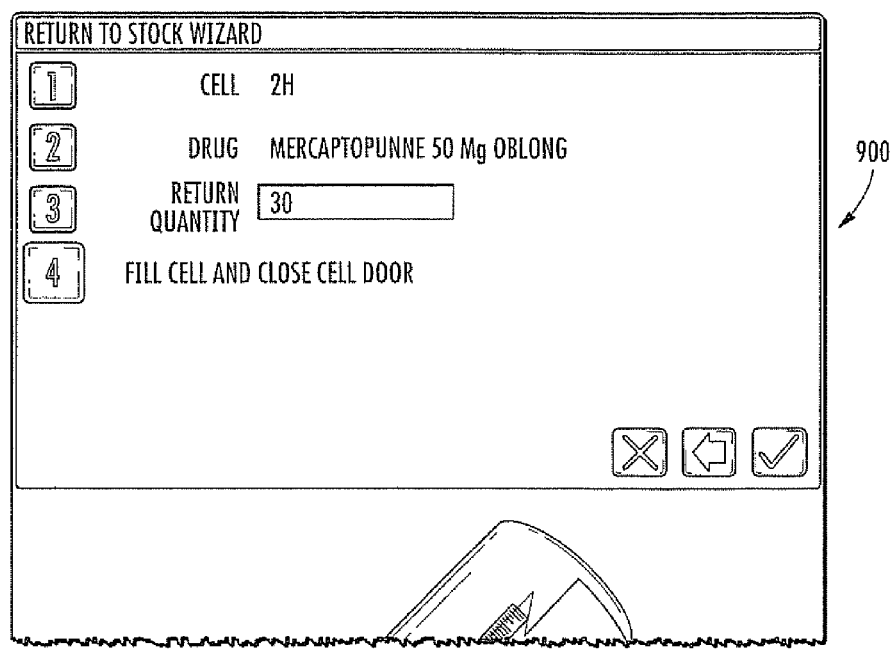
Figure 19A:
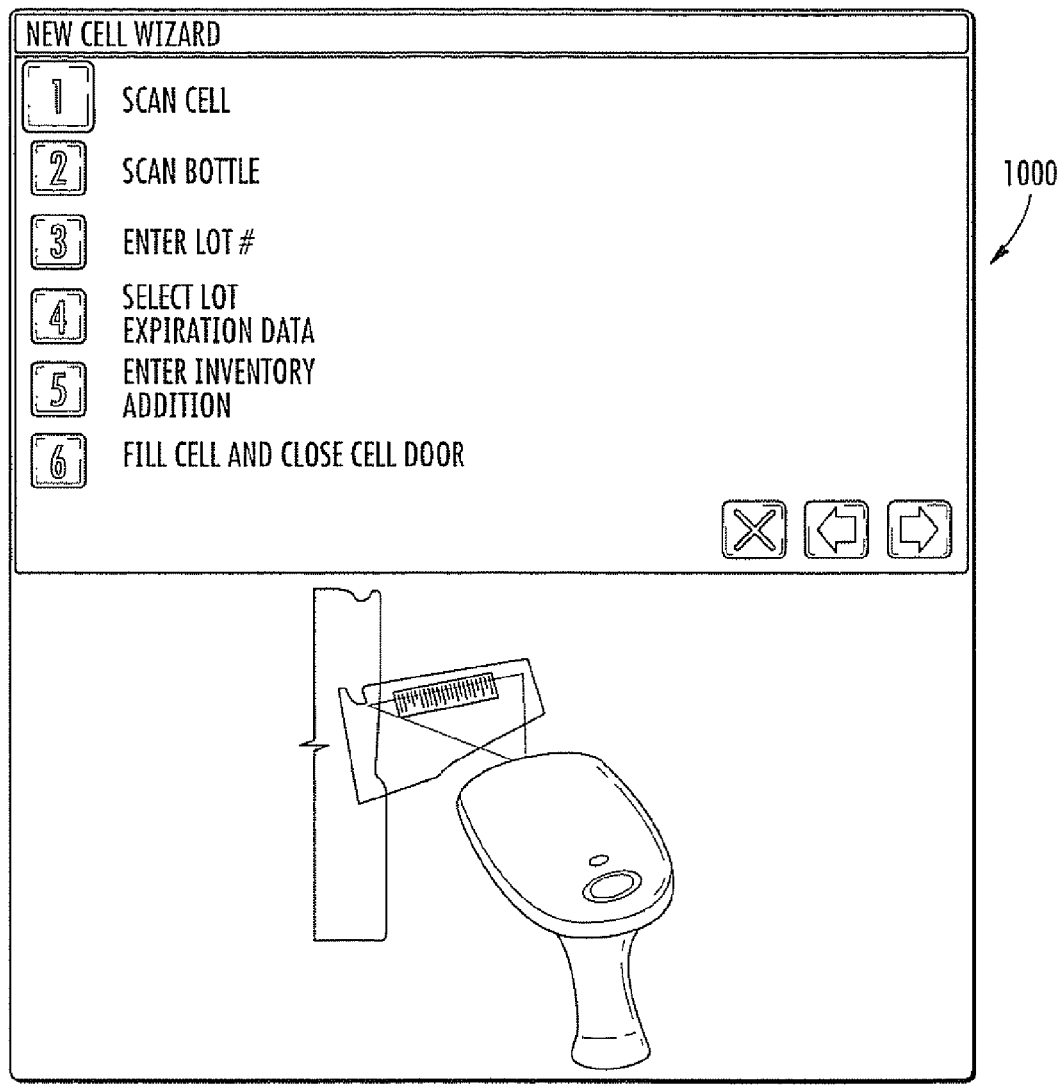
Figure 19B:
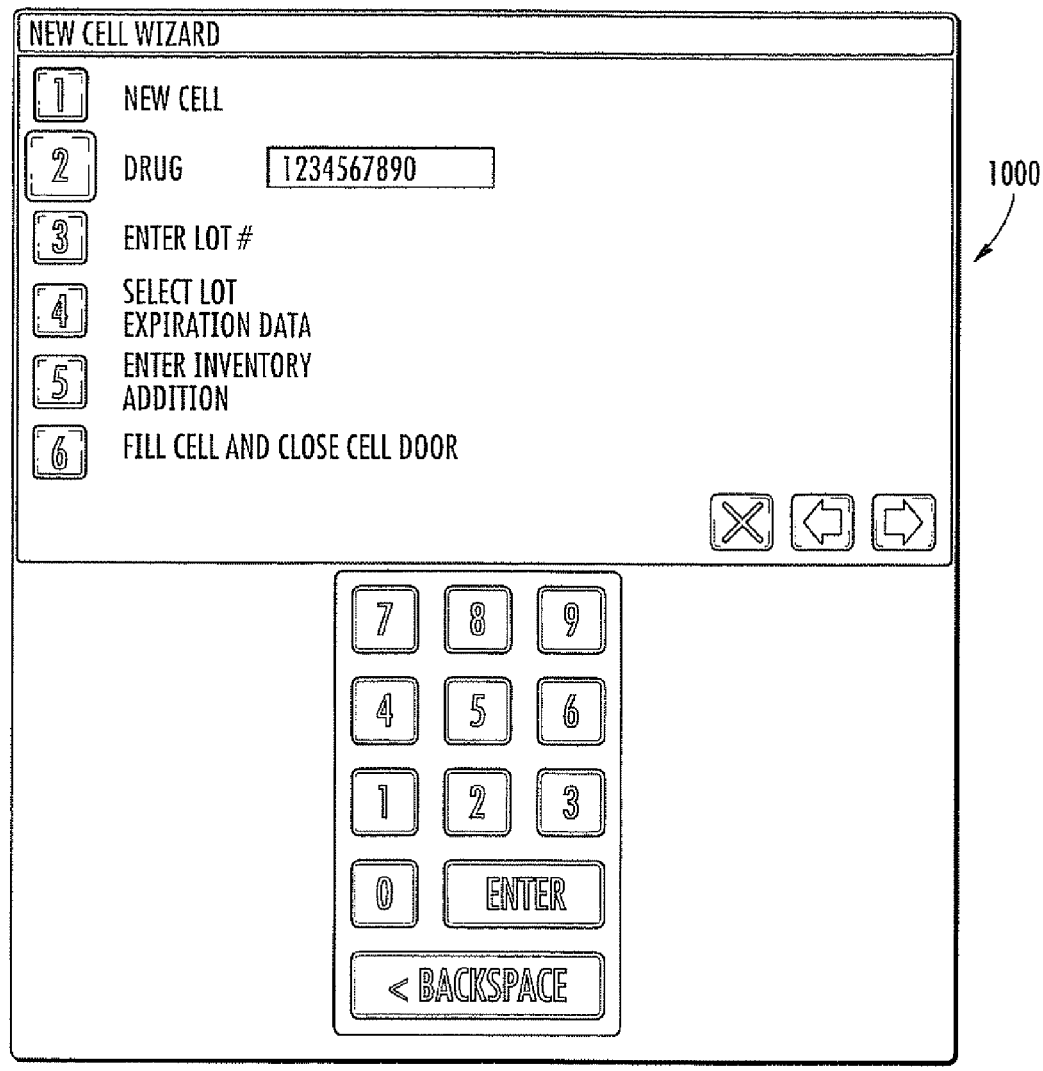
Figure 19C:
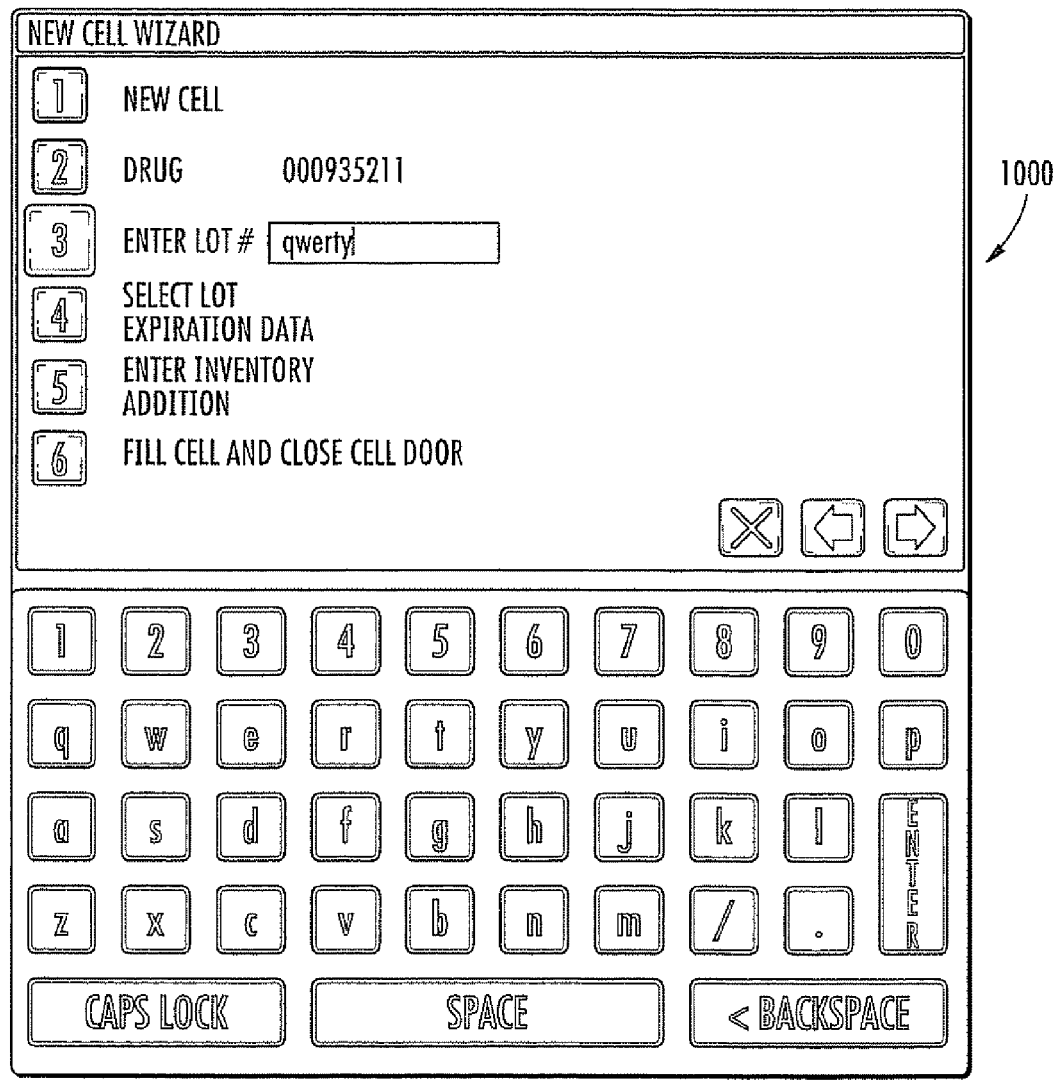
Figure 19E:
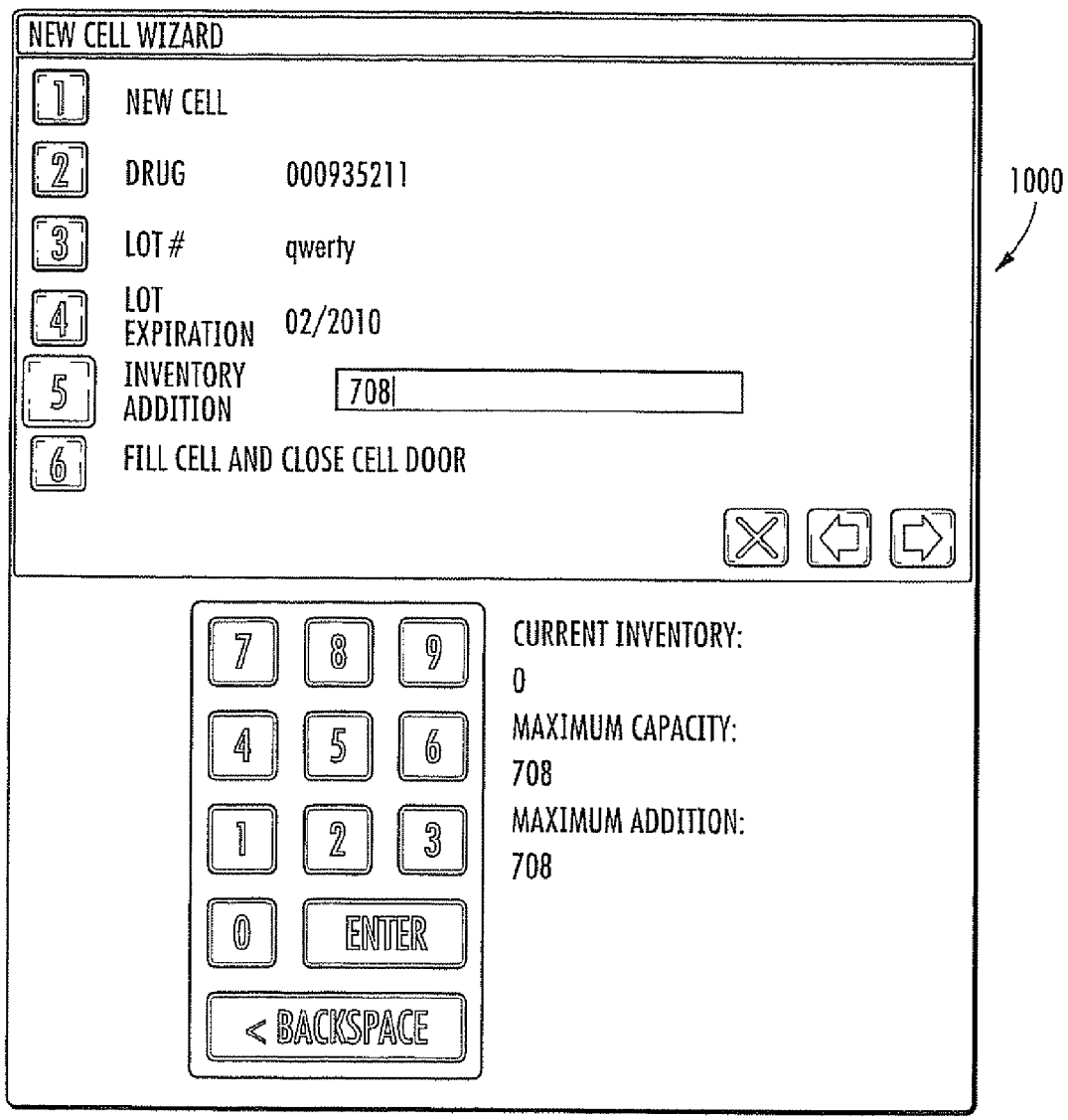
Figure 19F:
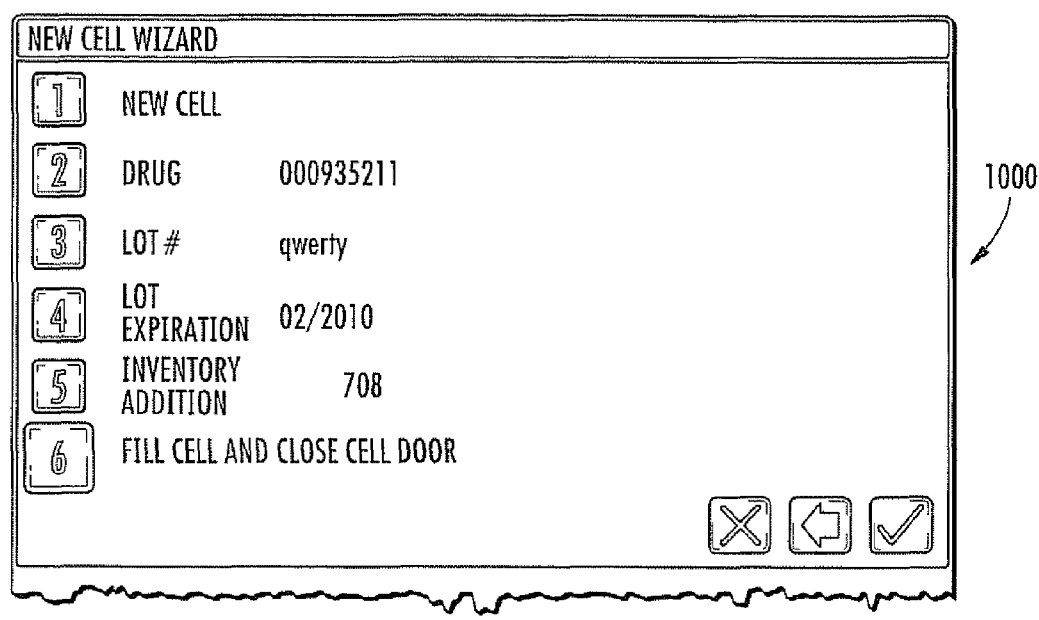

Referring now to FIGS. 18A-18C, the return-to-stock (RTS) wizard 900 will now be described. The RTS procedure is used to return partial prescription fills, calibration fills, and unclaimed prescription orders to the system 40. RTS procedures are performed on the replenishing side of the system 40. To perform an RTS procedure, a barcode on the pill container containing pills to be returned to stock is scanned, for example via scanner 50, and the RTS Wizard starts automatically. Alternatively, the user can open the RTS Wizard by touching the RTS Wizard GUI control 602*c* in the Parameters GUI 600. The indicator light flashes on the cell 100 from which the prescription was filled to identify to the operator the correct cell 100 for the pills being returned. The operator then scans a barcode associated with the identified cell 100. If the scan indicates that an operator is attempting to return pills to the wrong cell 100, an error message is displayed. The pill quantity is automatically calculated and displayed. The displayed value is the quantity of pills that were dispensed for this prescription order. For example, if only 9 pills were dispensed for a prescription order requiring 10 pills, the displayed return quantity is 9. The operator then empties the contents of the container into the correct cell 100. The operator then touches the complete GUI control to conclude operations.

New Cell Wizard

Referring now to FIGS. 19A-19F, a New Cell wizard 1000 is illustrated that is used for setting up and calibrating a cell 100 to house a drug already specified in the Master Drug List (MDL). The MDL is an internally maintained database of the pharmaceutical dispensing system 40 that includes all the drug dispensing information for each drug in the system's inventory. The New Cell wizard 1000 is launched via the New Cell GUI control 502c in the Cell Inventory GUI 500 (FIG. 13).

To set up a new cell, an operator launches the New Cell wizard via New Cell GUI control 502c. The cell door of the new cell 100 is opened and the bar code associated with the cell 100 is scanned via a barcode scanner associated with the pharmaceutical dispensing system 40. The bar code on the stock bottle is also scanned. Alternatively, the NDC of the drug can be entered manually via a pop-up keypad. The operator enters the Lot number of the drug, the Lot expiration date, and the pill quantity being added to the cell 100. The pills are then added to the cell 100 and the cell door is closed.

New Drug Wizard

Figure 20A:
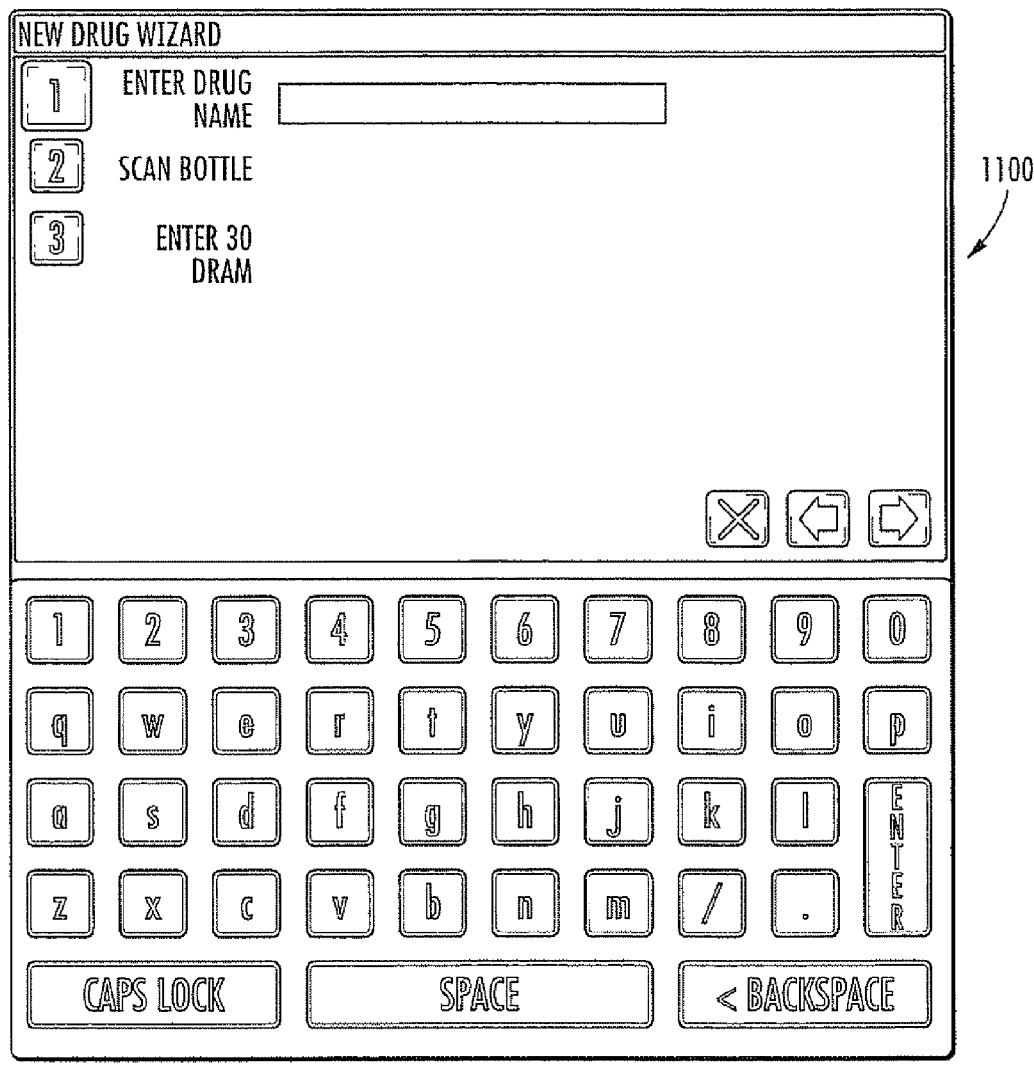
Figure 20B:
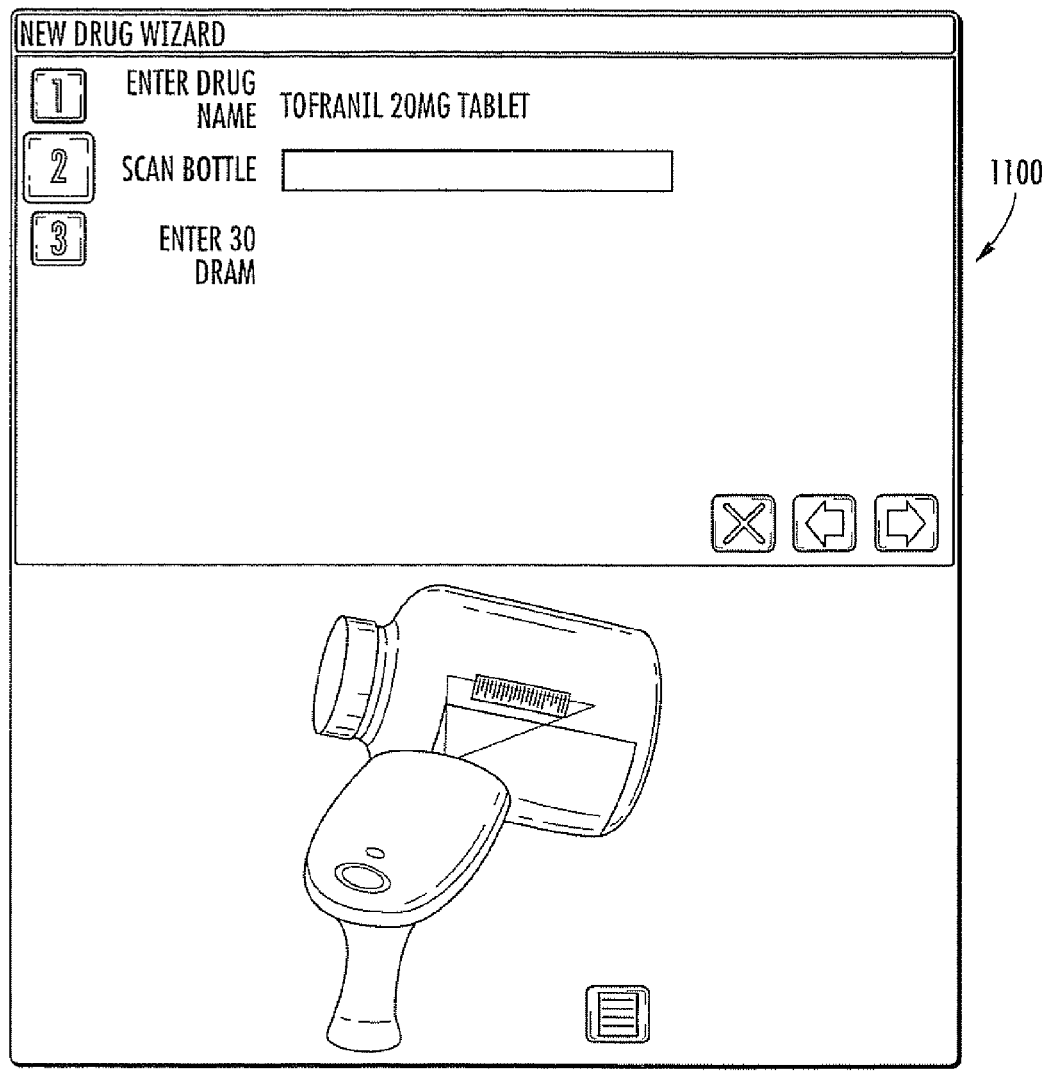
Figure 20C:
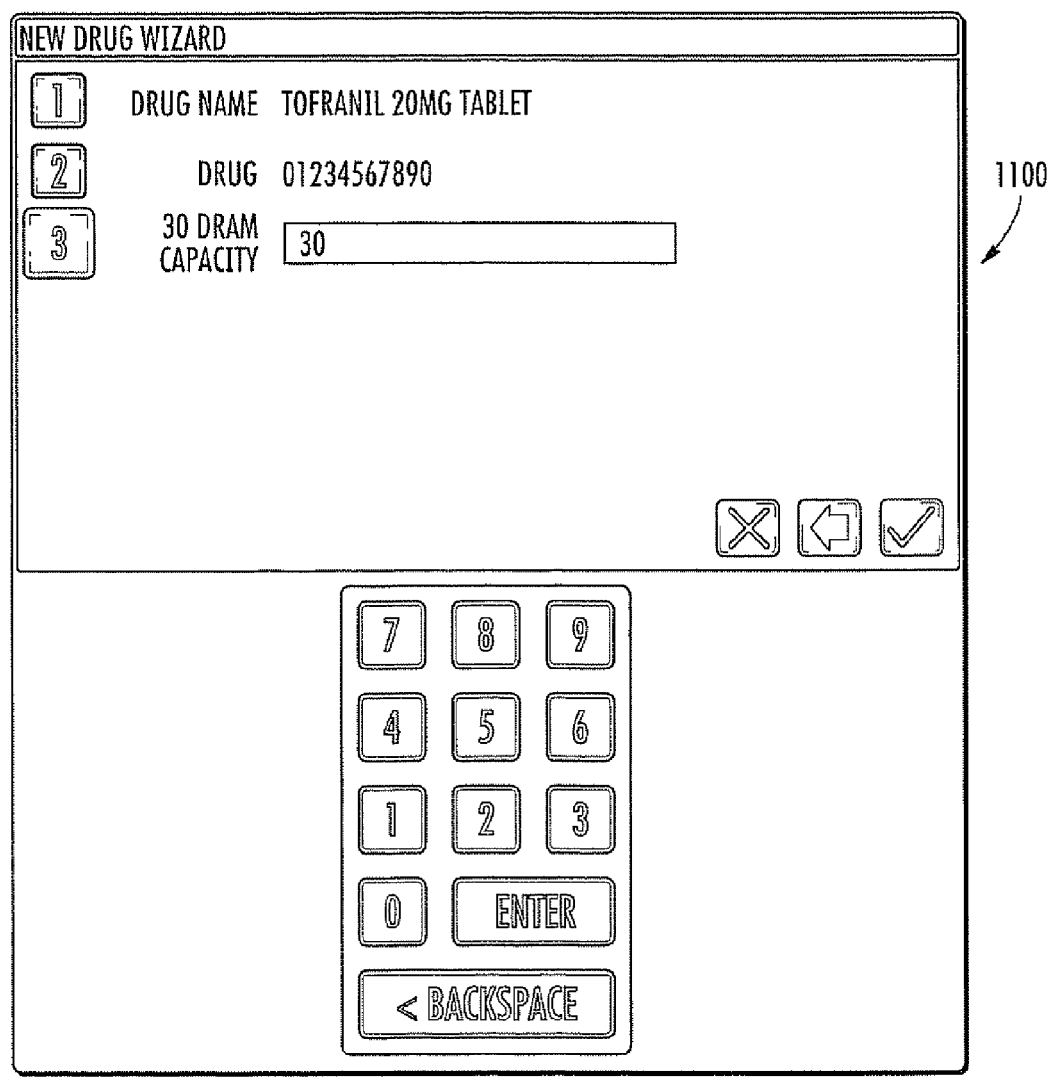

Referring now to FIGS. 20A-20C, adding a new drug to the system 40 will be described. An operator uses the New drug wizard 1100 to add a new drug to the pharmaceutical dispensing system 40. A new drug is one not currently described in the MDL of the pharmaceutical dispensing system 40. Operations for adding a new drug to the pharmaceutical dispensing system 40 are performed on the replenishing side of the system 40. A new drug can be added to inventory at any time including while the pharmaceutical dispensing system 40 is in run mode and processing prescription orders.

The various steps of adding a new drug are numbered on the left hand side of the various add drug wizard GUIs, as illustrated (FIGS. 20A-20C). From the Cell Inventory GUI 500, an operator touches the New Drug Wizard GUI control 502b. The operator then enters the drug name using the pop-up keyboard. The new drug wizard then directs the operator to scan the barcode on the stock bottle via a barcode scanner associated with the pharmaceutical dispensing system 40, or to touch the NDC GUI control and enter the NDC manually using the pop-up keyboard. The operator then enters the thirty Dram capacity for the drug using the pop-up keypad (thirty dram capacity is required so that the system 40 can calculate how many pill containers are needed to fill any given prescription order based on the number of pills ordered).

Reports

The pharmaceutical dispensing system 40 includes a reports component, which allows an operator to build, run, export, and print reports. Exemplary reports are identified in Table 1 below. However, embodiments of the present invention are not limited to the identified reports.

TABLE 1

| Report | Description |
| --- | --- |
| Audit Cell | Displays any changes to cell parameters by operator. |
| Audit Drug | Displays any changes to drug parameters by operator. |
| Cell Settings | Lists all active cells and their current calibration status and dispensing parameters (baffle, height, width, and pressure). |
| Dispense Info | Lists prescription orders filled by the pharmaceutical dispensing system during a designated date range. |
| Drug Prescription History | Lists all drugs dispensed by the pharmaceutical dispensing system during a designated interval. |
| Drug Setup | Displays all cells that were set up with a drug during a designated interval. |
| Inventory by Cell | Displays the inventory for each cell in the pharmaceutical dispensing system. |
| Inventory by Drug Code | Displays the pharmaceutical dispensing system's inventory by drug code. |
| Lot Usage | Lists all prescription orders and the Lot number used to fill each prescription order for a given drug code. If a Lot number is specified, this report lists only those orders filled with the given drug code and Lot number. |
| Low Cell | Lists all cells with inventory less than the drug's low inventory threshold. |
| Non-Calibrated Cells | Lists all active cells for which a calibration fill has not yet been successfully completed. |
| Operator Actions | Displays certain actions performed on the unit by a given operator during a specified time range. |
| Order Detail | Displays all details for a specific prescription order. These include the states the order passed through in the unit, dispensing cell information and dispensing shelf location. |
| Replenish Info | Lists all replenishments and Return to Stock procedures. |
| Replenishments by Day | On a bar graph, displays a replenishment count grouped by hour for a specified day. |
| Prescription Volume by Day | On a bar graph, displays a count of prescription orders submitted to the pharmaceutical dispensing system and prescriptions picked up from the pharmaceutical dispensing system, grouped by hour for a specified day. |
| Prescription Volume by Drug Code | Displays a summary of the number of dispensed pills and prescriptions, grouped by drug code and a time period (day/month/year). |

Referring to FIGS. 21A-21G, operations for building, running, viewing, exporting, and printing reports (e.g., any of the reports listed in Table 1), according to some embodiments of the present invention will be described. Although the output of each report is different, the steps that an operator takes to generate a report generally are the same. These steps, broadly speaking, are build the report, view the report, set up a printer and print the report. Each of these steps are described below.

Table 2 below contains a description of column headings that are utilized in various ones of the reports that can be built, according to some embodiments of the present invention.

However, embodiments of the present invention are not limited to the listed column headings. Other column headings may also be utilized in various embodiments of the present invention.

TABLE 2

| Column Heading | Description |
| --- | --- |
| Drug Code | The drug's NDC or DIN. |
| Drug Name | The name of the drug. |
| Entry date | Date prescription order was processed by the pharmaceutical dispensing system. |
| Loc. | Cell location. The cell ID (for example, 2B). |
| Lot Exp. | Expiration date of the stock bottle's Lot. |
| NDC Barcode | Bar code on the stock bottle identifying the drug's NDC value. Bar codes displayed in this column can be scanned via scanner. |
| Order No. | The prescription order number. |
| Qty. | Number of pills dispensed to fill a specific prescription order. |
| Vial No. | The number of vials needed to contain all of the pills for a prescription order. |
| Total Qty | Total number of pills dispensed per prescription order. |
| Script Total | Total number of prescriptions for a given drug. |
| Date Filled | Date prescription order was filled. |
| Script Count | Number of prescriptions filled for a given drug code. |
| Avg Pills/Script | Average number of pills per prescription for a given drug code. |
| Total Fill Qty | Total number of pills dispensed for a given drug code. |
| Replenish Date | Date a given cell was replenished. |
| Orig Qty | Original inventory in a cell when it was replenished. |
| Add Qty | Pill inventory added to a cell when it was replenished. |
| New Qty | Resulting inventory after a cell was replenished (Orig Qty + Add Qty). |
| Max Cap | The maximum established capacity for a cell that was replenished. |
| % Repl | Of the available pill capacity in a cell, the percentage that was replenished. |
| Total Qty. | Total number of pills dispensed for a particular drug. |
| Total Scripts | Total number of prescriptions processed for a particular drug. |

Figure 21A:
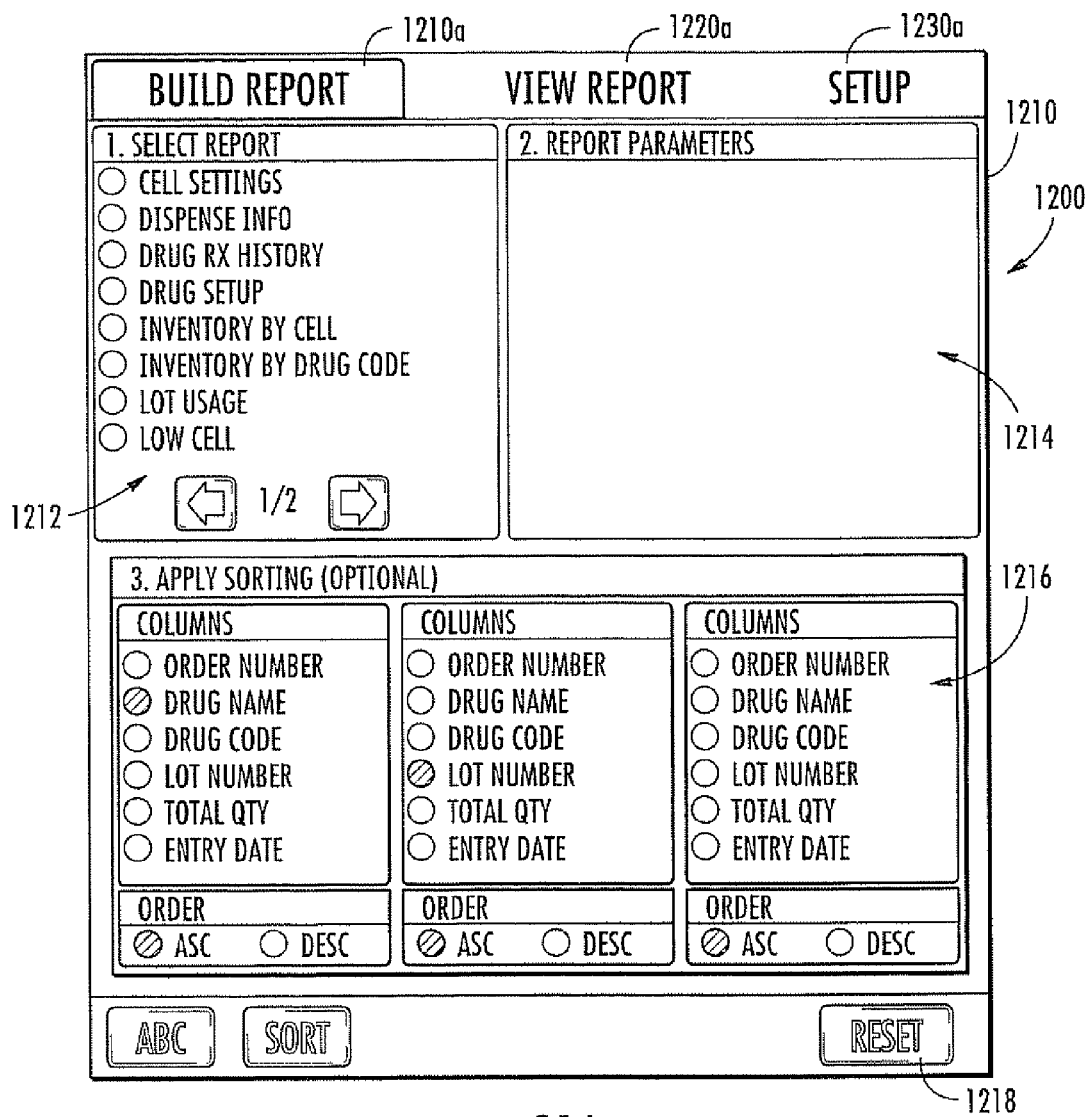
FIGS. 21A-21G are GUIs that allow an operator of the pharmaceutical dispensing system of FIGS. 2-3 to build, view, print and export various reports, in accordance with some embodiments of the present invention.

According to some embodiments of the present invention, an operator builds a report on the dispensing side of the pharmaceutical dispensing system 40 by activating the System Functions GUI control 430b in the Home GUI 400 and then activating a "launch" GUI control that is displayed. In response, a reports GUI 1200 is displayed as illustrated in FIG. 21A. An operator may also build reports on the replenishing side of the automated pharmacy system 40 by activating a System Functions GUI (or similar GUI control) in any of the replenishing side GUIs described above.

Figure 21B:
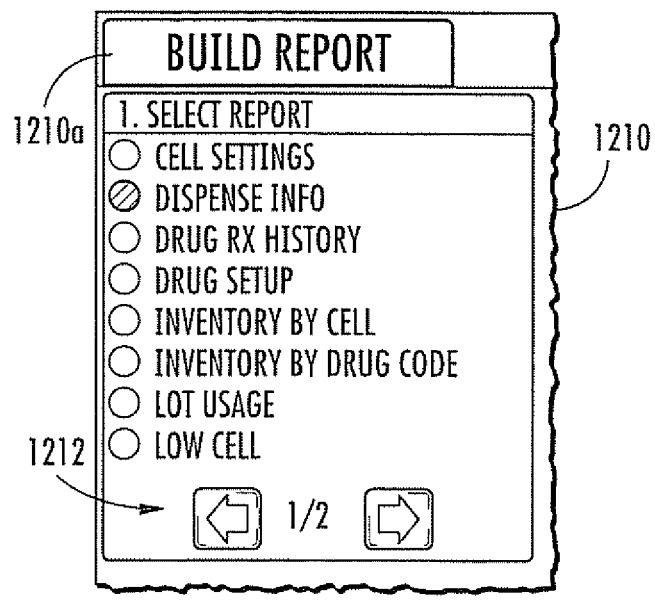

In the illustrated embodiment, the reports GUI 1200 shown in FIG. 21A includes three separate GUIs: Build Report 1210, View Report 1220, and Setup 1230. Each of these GUIs is displayed when an operator touches a respective tab 1210a, 1220a, 1230a, as illustrated. The Build Report GUI 1210 has three separate elements: Select Report 1212, Report Parameters 1214, and Apply Sorting 1216. The Select Report element 1212 displays a list of reports that an operator can select. To build a report, an operator selects a report from this list, as illustrated in FIG. 21B. In FIG. 21B, the operator has selected the "Dispense Info" report.

Figure 21C:
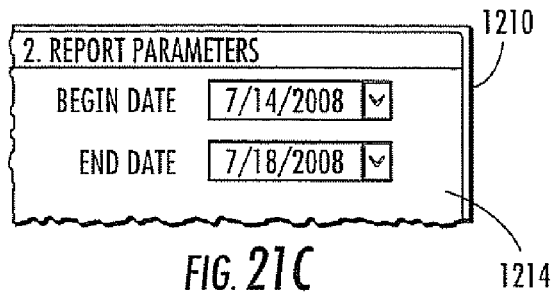
Figure 21D:
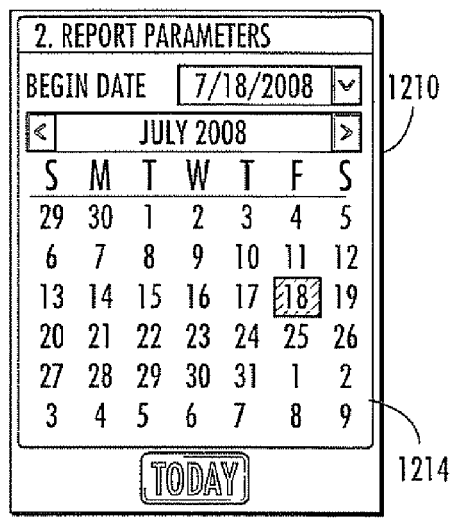

After selecting a report, the report parameters, such as begin date and end date, are defined in the Report Parameters element 1214, as illustrated in FIG. 21C. Not all reports have selectable parameters, however. In the illustrated report, an operator is selecting a date range for the "Dispense Info" report. The "Dispense Info" report will display all of the prescription orders filled by the pharmaceutical dispensing system 40 during the specified time period. As illustrated in FIG. 21D, a pop-up calendar can be displayed for use in selecting begin dates and end dates.

Figure 21E:
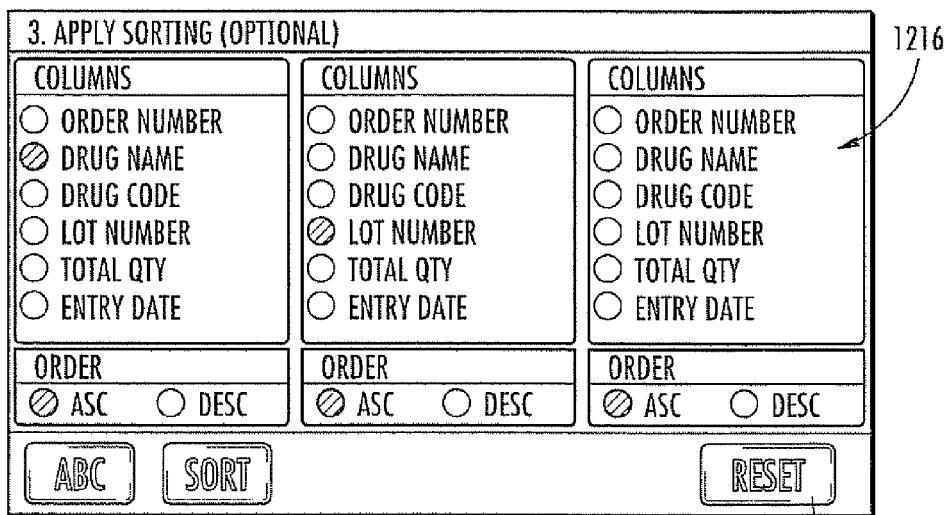

Referring to FIG. 21E, the Apply Sorting element 1216 may be utilized to sort the output of various columns of a selected report (e.g., ascending order, descending order, etc.). In the illustrated Apply Sorting element 1216 displayed in FIG. 21E, the operator has decided to sort by drug name in ascending order, and to sort by drug lot number in ascending order. The Reporting GUI displayed in FIG. 21E also includes a Reset GUI control 1218 that allows an operator to start over and reenter desired sorting and report parameter criteria. When sorting with multiple columns, as illustrated in FIG. 21E, sorting is performed from left to right, according to some embodiments of the present invention. For example, if an operator selects "Entry Date" in the first column of FIG. 21E, and selects "Drug Code" in the second column of FIG. 21E, a report will be sorted such that drug codes for each entry date will be displayed. Further, if an operator selects "Lot Number" in the third column of FIG. 21E, the above-described report will be sorted such that lot numbers for each drug code will be displayed. In other words, for each entry date, a list of drug codes will be displayed, and for each drug code, a list of lot numbers will be displayed. Embodiments of the present invention, however, are not limited to this type of sorting. Various ways of sorting information for reports may be utilized without limitation.

Figure 21F:
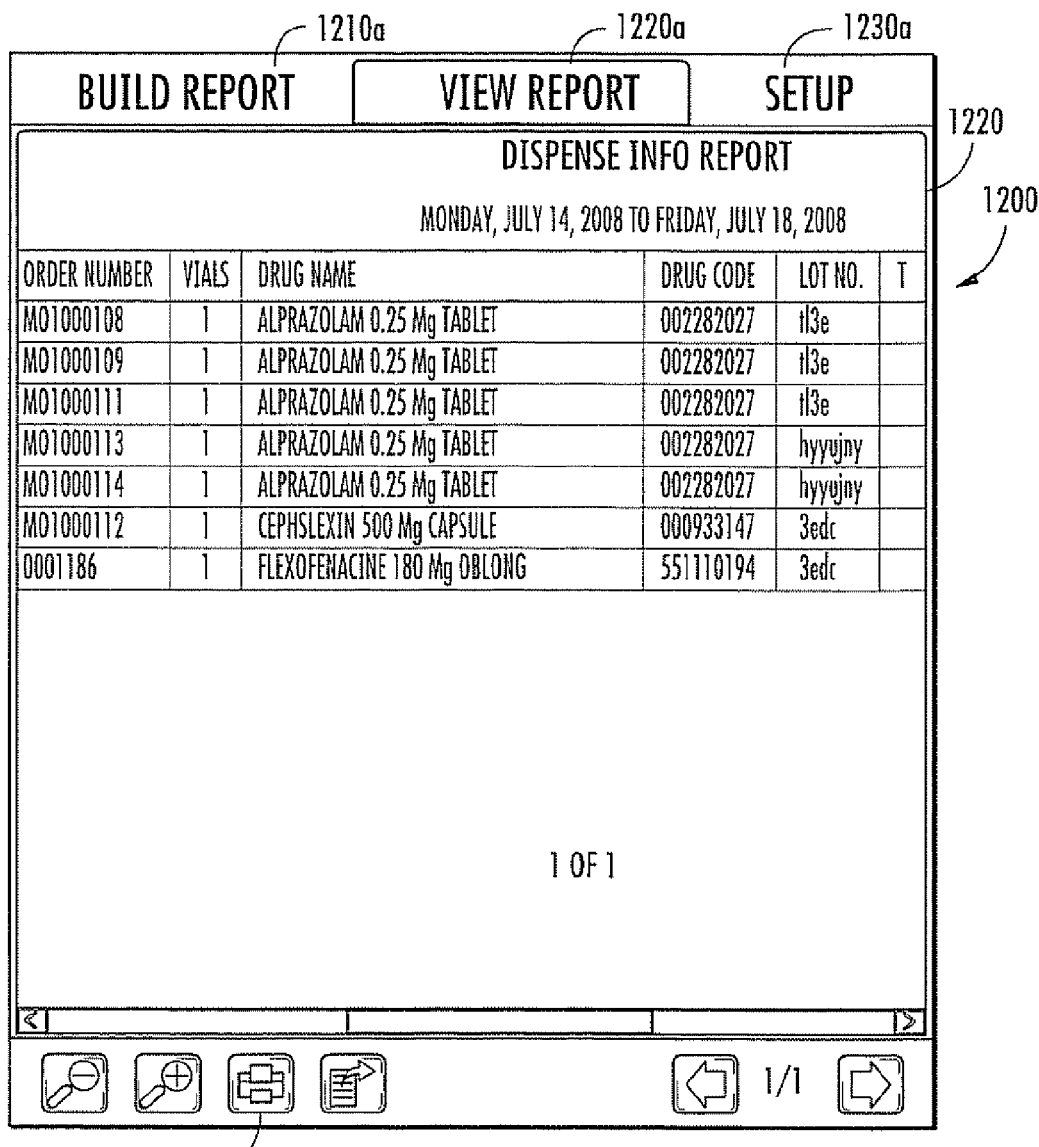

Once a report is built it can be viewed by touching the View Report tab 1220a, which displays the View Report GUI 1220, as illustrated in FIG. 21F. The operator can manipulate vertical and horizontal scroll bars that are provided when a report is displayed to view hidden regions of the report, as would be understood by those skilled in the art. In addition, zoom-in and zoom-out tools are provided to enlarge and reduce the displayed size of a report.

Figure 21G:
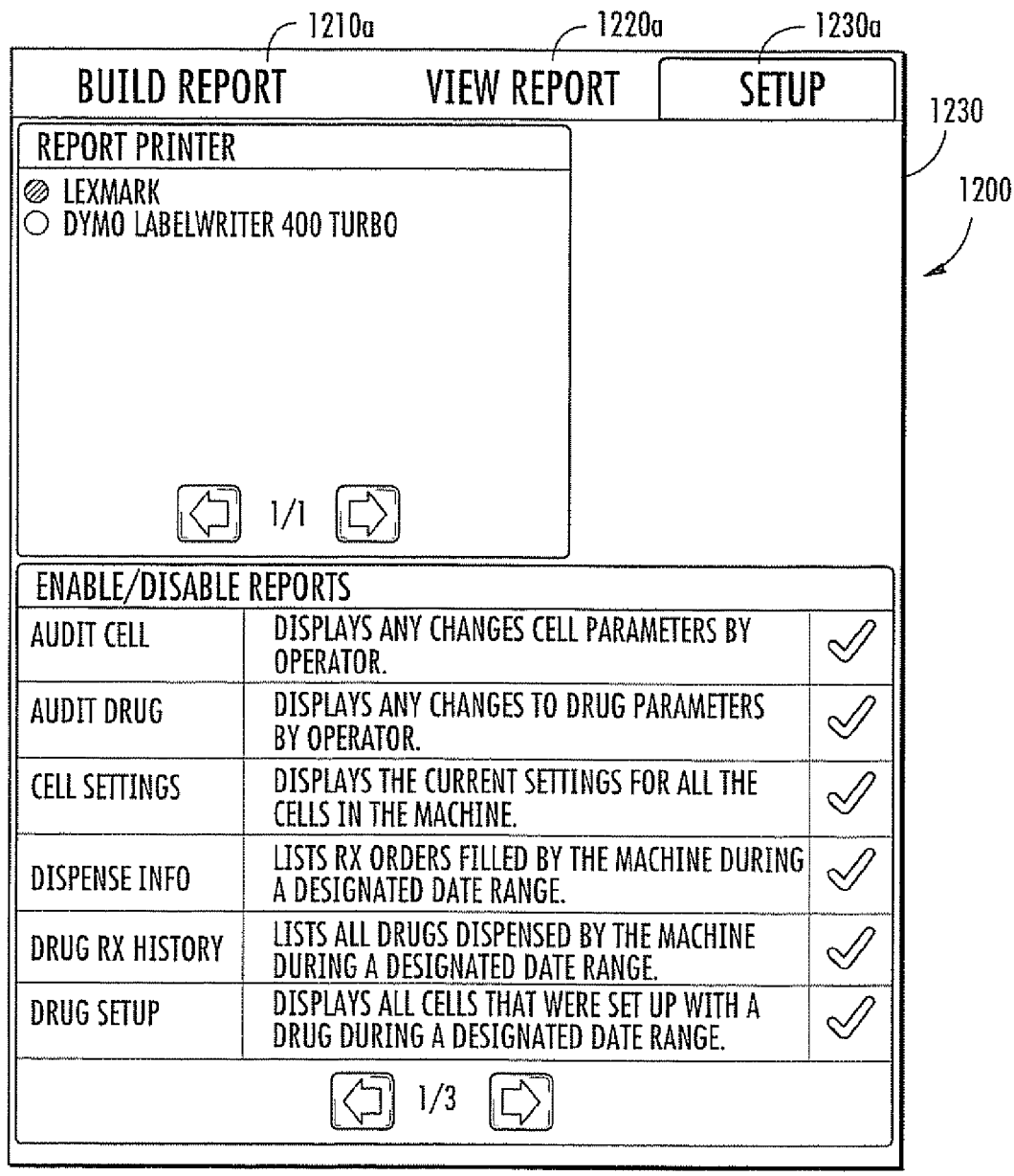

At this point, an operator can choose to print the viewed report or to run the report again with different parameters. To run the report with different parameters, the operator touches the Build Report tab 1210a, which displays the Build Report GUI 1210, selects new parameters, and touches the View Report tab 1220a, which displays the View Report GUI 1220, to rerun the report. To print the viewed report, the operator touches the print GUI control 1240. However, prior to printing, the operator needs to designate a printer using the Setup GUI 1230. To designate a printer, the operator touches the Setup tab 1230*a*, which displays the Setup GUI 1230, and then selects a printer from the Select Printer GUI 1250, as illustrated in FIG. 21G.

Reports can also be exported to other applications and printed from those applications. For example, a report can be exported to a spreadsheet application. When an operator chooses to export a report, the report format is rendered in comma-separated format and is saved to a pre-designated location on the pharmaceutical dispensing system 40. The pharmaceutical dispensing system 40 uniquely names each exported file. In some embodiments, an exported file is saved in ".csv format" in the form <ReportName_Date_TimeStamp>. However, embodiments of the present invention are not limited to a particular file format for exporting. Other file formats may be utilized.

Device Relationship Management (DRM)

The pharmaceutical dispensing system 40 includes a Device Relationship Management (DRM) component, which provides the following: health monitoring functions for the pharmaceutical dispensing system 40; local DRM data storage; and a guaranteed data delivery mechanism. Information about the health of the pharmaceutical dispensing system 40 is gathered by a variety of health monitoring functions, which report sensor values (particularly during critical portions of operation of the system 40), error occurrences, results of periodically performed built-in-tests, and high level machine events.

Sensors may be configured to monitor temperature and/or pressure of various components of the pharmaceutical dispensing system 40. In addition, the number and/or percent of prescription order filling failures can be monitored. High level machine events can include counting problems, power outages, etc. Built-in tests that can be performed include a system health test that automatically runs on start up to check all of the components of the pharmaceutical dispensing system 40.

This information is held as time-stamped data in a Local DRM Data Storage facility, specifically a SQL Server Database. The guaranteed data delivery mechanism is implemented as part of a software service that pulls information from the database and either a) transmits it over a secure network connection; or b) downloads it to a removable medium, such as a flash drive.

Figure 22:
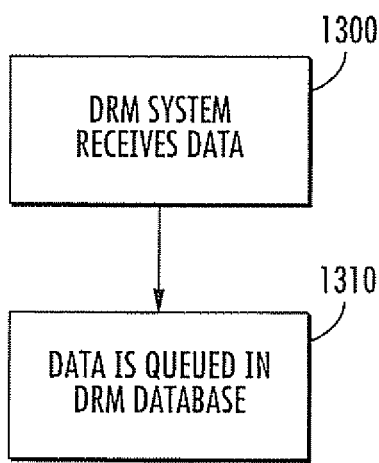
FIGS. 22-23 are flow charts illustrating operations of a Device Relationship Management (DRM) component for the pharmaceutical dispensing system of FIGS. 2-3, in accordance with some embodiments of the present invention.
Figure 23:
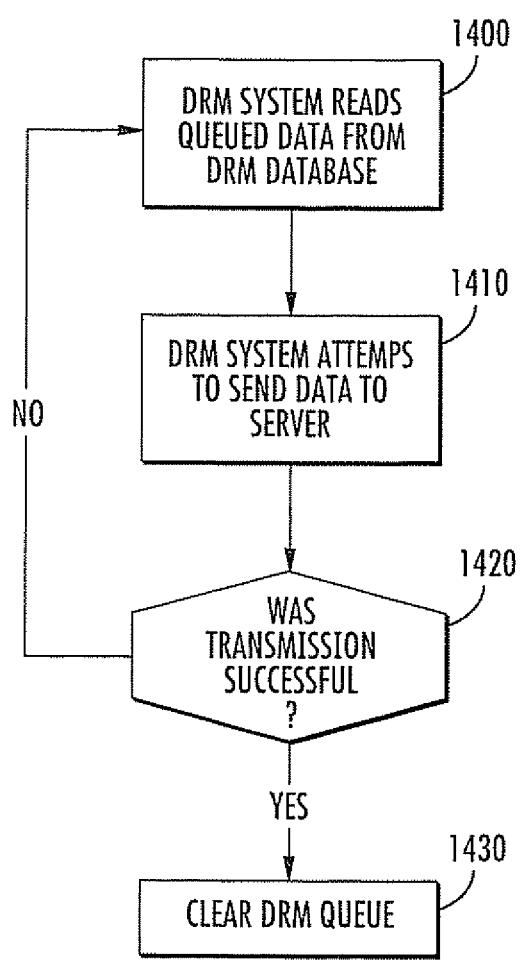

Referring to FIGS. 22-23, the DRM system also includes a reliable message delivery system. This system guarantees that in the event of a network outage, power outage, or other situation which causes the system to be unable to send data, no data will be lost until the outage is resolved. When data is received (Block 1300), it is queued in a database (Block 1310). The system reads queued data from the DRM database (Block 1400) and attempts to send the data back to the DRM server (Block 1410). If the transmission was successful and receipt is acknowledged (Block 1420), the data is removed from the queue (Block 1430); otherwise, the data remains in the queue and transmission is retried at the next opportunity.

Figure 24:
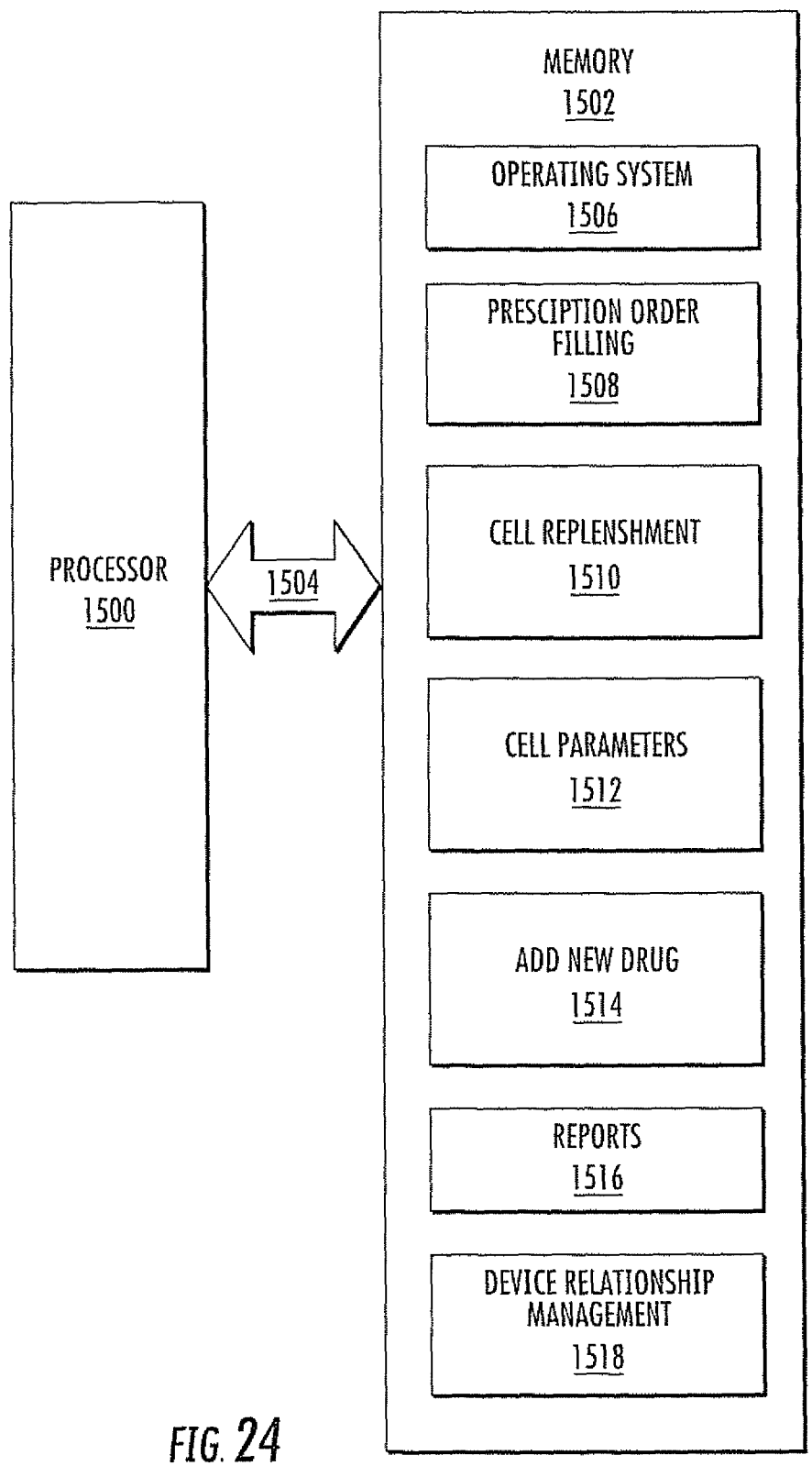
FIG. 24 is a block diagram that illustrates a software architecture for implementing operations of the pharmaceutical dispensing system of FIGS. 2-3, in accordance with some embodiments of the present invention.

FIG. 24 illustrates a processor 1500 and a memory 1502 that may be used to implement the operations of the pharmaceutical dispensing system 40 of FIGS. 2-3, according to some embodiments of the present invention. For example, in some embodiments of the present invention, the processor 1500 and memory 1502 may be used to embody the processors and the memories used in automatically filling prescription orders, in replenishing pills within cells 100, in modifying parameters of cells 100, in adding new drugs to inventory, in creating reports, etc.

The processor 1500 communicates with the memory 1502 via an address/data bus 1504. The processor 1500 may be, for example, a commercially available or custom microprocessor. The memory 1502 is representative of the overall hierarchy of memory devices containing the software and data used to automatically fill prescription orders, to replenish pills within cells 100, to modify parameters of cells 100, and to add new drugs to inventory, to generate reports, and to perform device relationship management, in accordance with some embodiments of the present invention. The memory 1502 may include, but is not limited to, the following types of devices: cache, ROM, PROM, EPROM, EEPROM, flash, SRAM, and DRAM.

As shown in FIG. 24, the memory 1502 may hold seven or more major categories of software and data: an operating system 1506, a prescription order filling module 1508, a cell replenishment module 1510, a cell parameters module 1512, an add new drug module 1514, a reports module 1516, and a Device Relationship Management (DRM) module 1518. The operating system 1506 controls operations of the prescription order filling module 1508, cell replenishment module 1510, cell parameters module 1512, add new drug module 1514, reports module 1516, and DRM module 1518.

The prescription order filling module 1508 comprises logic for processing prescription orders as described above with respect to the various dispensing side GUIs. The cell replenishment module 1510 comprises logic for monitoring/controlling/modifying drug inventory in each of the cells 100, as described above with respect to the various replenishing side GUIs. The cell parameters module 1512 comprises logic for monitoring/controlling/modifying parameters for each of the cells 100, as described above with respect to the various replenishing side GUIs. The add new drug module 1514 comprises logic for adding a new drug to a cell 100, as described above with respect to the various replenishing side GUIs. The reports module 1516 comprises logic for building, running, exporting, and printing reports from either side of the pharmaceutical dispensing system 40, as described above with respect to FIGS. 21A-21G. The DRM module 1518 comprises logic for handling and transmitting data to and from the pharmaceutical dispensing system 40, as described below with respect to FIGS. 22-23.

Although FIG. 24 illustrates an exemplary software architecture that may facilitate automatically filling prescription orders, replenishing pills within cells 100, modifying parameters of cells 100, adding a new drug to inventory, generating reports, and performing device relationship management functions, it will be understood that the present invention is not limited to such a configuration, but is intended to encompass any configuration capable of carrying out the operations described herein.

Computer program code for carrying out operations of the prescription order filling module 1508, cell replenishment module 1510, cell parameters module 1512, add new drug module 1514, reports module 1516, and DRM module 1518 may be written in a high-level programming language, such as Python, Java, C, and/or C++, for development convenience. In addition, computer program code for carrying out operations of embodiments of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A pharmaceutical dispensing system, comprising:
   a frame having first and second opposed sides;
   a plurality of cells configured to house pharmaceutical pills, each of the cells being accessible from the first side of the frame for replenishment of pharmaceutical pills therein;
   a plurality of chutes, each of the chutes connected to and associated with a respective one of the plurality of cells, each of the chutes being accessible from the second side of the frame for dispensing of pharmaceutical pills;
   a first touch screen display on the frame first side;
   a second touch screen display on the frame second side;
   a processor;
   memory coupled to the processor;
   a computer program residing in the memory that is executable by the processor for displaying a cell inventory graphical user interface (GUI) within the first touch screen display, wherein the cell inventory GUI displays cell inventory information, and wherein the cell inventory GUI comprises one or more GUI controls that are responsive to user touching for adding and/or modifying contents of the cells; and
   a computer program residing in the memory that is executable by the processor for displaying a prescription processing GUI within the second touch screen display, wherein the prescription processing GUI displays an array of chute icons, wherein each chute icon corresponds to a respective chute and displays an identification of the respective chute, wherein each chute icon is expandable to an enlarged chute icon display size in response to user touching thereof, wherein each chute icon is configured to display a number of pills contained within the respective chute when in the enlarged display size, and wherein each chute icon is displayed with a graphic effect that indicates a status of a prescription order for the respective chute.

2. The system of claim 1, wherein a record for each prescription order in a queue for the respective chute is displayed in the prescription processing GUI in response to a user touching the chute icon corresponding to the respective chute, and wherein each record comprises status information for the corresponding prescription order.

3. The system of claim 2, wherein each prescription order record is displayed with a graphic effect that indicates the status of a respective prescription order.

4. The system of claim 3, wherein the prescription order record graphic effect comprises a color.

5. The system of claim 1, wherein each chute icon comprises a border and wherein the border is displayed with a graphic effect that indicates the status of a prescription order for the respective chute.

6. The system of claim 5, wherein the graphic effect comprises a color.

7. The system of claim 1, wherein each chute icon displays indicia that indicate that a prescription order is ready in the respective chute.

8. The system of claim 1, wherein each chute icon displays indicia that indicate that a prescription order for the respective chute is incomplete.

9. The system of claim 1, wherein a representation of each cell in the cell inventory GUI is displayable in a color that indicates an inventory level of pharmaceutical pills in a corresponding cell.

10. The system of claim 1, further comprising a computer program residing in the memory that is executable by the processor for displaying a report builder GUI within the first and second touch screen displays, wherein the report builder GUI is configured to build reports relating to one or more of the following: pending prescription orders, filled prescription orders, cell inventory information, and drug information.

11. The system of claim 1, further comprising a computer program residing in the memory that is executable by the processor for monitoring selected functions of the pharmaceutical dispensing system and for storing selected parameters associated with the monitored functions.

12. A pharmaceutical dispensing system, comprising:
   a frame having first and second opposed sides;
   a plurality of cells configured to house pharmaceutical pills, each of the cells being accessible from the first side of the frame for replenishment of pharmaceutical pills therein;
   a plurality of chutes, each of the chutes connected to and associated with a respective one of the plurality of cells, each of the chutes being accessible from the second side of the frame for dispensing of pharmaceutical pills;
   a touch screen display on the frame second side;
   a touch screen display on the frame first side;
   a processor;
   memory coupled to the processor;
   a computer program residing in the memory that is executable by the processor for displaying a prescription processing GUI within the touch screen display, wherein the prescription processing GUI displays an array of chute icons, wherein each chute icon corresponds to a respective chute and displays an identification of the respective chute, wherein each chute icon is expandable to an enlarged chute icon display size in response to user touching thereof, wherein each chute icon is configured to display a number of pills contained within the respective chute when in the enlarged display size, and wherein each chute icon is displayed with a graphic effect that indicates the status of a prescription order for the respective chute; and
   a computer program residing in the memory that is executable by the processor for displaying a cell inventory graphical user interface (GUI) within the touch screen display on the frame first side, wherein the cell inventory GUI displays cell inventory information, and wherein the cell inventory GUI comprises one or more GUI controls that are responsive to user touching for adding and/or modifying contents of the cells.

13. The system of claim 12, wherein a record for each prescription order in a queue for the respective chute is displayed in the prescription processing GUI in response to a user touching the chute icon corresponding to the respective chute, and wherein each record comprises status information for the corresponding prescription order.

14. The system of claim 13, wherein each prescription order record is displayed with a graphic effect that indicates the status of the corresponding prescription order.

15. The system of claim 12, wherein a representation of each cell in the cell inventory GUI is displayable in a color that indicates an inventory level of pharmaceutical pills in a corresponding cell.

16. The system of claim 12, further comprising a computer program residing in the memory that is executable by the processor for displaying a report builder GUI within the first and second touch screen displays, wherein the report builder GUI is configured to build reports relating to one or more of the following: pending prescription orders, filled prescription orders, cell inventory information, and drug information.

17. The system of claim 12, further comprising a computer program residing in the memory that is executable by the processor for monitoring selected functions of the pharmaceutical dispensing system and for storing selected parameters associated with the monitored functions.

* * * * *

UNITED STATES PATENT AND TRADEMARK OFFICE
CERTIFICATE OF CORRECTION

PATENT NO.        : 8,972,050 B2                                    Page 1 of 1
APPLICATION NO.   : 12/466717
DATED             : March 3, 2015
INVENTOR(S)       : Johnson et al.

It is certified that error appears in the above-identified patent and that said Letters Patent is hereby corrected as shown below:

In the Specification:
Column 1, Line 43: Please correct "and 6,1767392"
　　　　　　　　　　to read -- and 6,176,392 --

Signed and Sealed this
Twenty-first Day of July, 2015

Michelle K. Lee
*Director of the United States Patent and Trademark Office*